(12) United States Patent
Ghosh et al.

(10) Patent No.: US 6,835,938 B2
(45) Date of Patent: Dec. 28, 2004

(54) BIOPOLYMER ARRAY SUBSTRATE THICKNESS DEPENDENT AUTOMATED FOCUS-DISTANCE DETERMINATION METHOD FOR BIOPOLYMER ARRAY SCANNERS

(75) Inventors: Jayati Ghosh, San Jose, CA (US); John F. Corson, Stanford, CA (US); Debra A. Sillman, Los Altos, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 196 days.

(21) Appl. No.: 10/210,855

(22) Filed: Jul. 31, 2002

(65) Prior Publication Data

US 2004/0021091 A1 Feb. 5, 2004

(51) Int. Cl.[7] ................................................. G01N 21/64
(52) U.S. Cl. ................................................... 250/458.1
(58) Field of Search ..................................... 250/458.1

(56) References Cited

U.S. PATENT DOCUMENTS

| | | | |
|---|---|---|---|
| 5,091,652 A | 2/1992 | Mathies et al. | |
| 5,260,578 A | 11/1993 | Bliton et al. | |
| 5,296,700 A | 3/1994 | Kumagai | |
| 5,324,633 A | 6/1994 | Fodor et al. | |
| 5,585,639 A | 12/1996 | Dorsel et al. | |
| 5,760,951 A | 6/1998 | Dixon et al. | |
| 5,763,870 A | 6/1998 | Sadler et al. | |
| 6,078,390 A | 6/2000 | Bengtsson | |
| 6,084,991 A | 7/2000 | Sampas | |
| 6,222,664 B1 | 4/2001 | Dorsel | |
| 6,284,465 B1 | 9/2001 | Wolber | |
| 6,320,196 B1 | 11/2001 | Dorsel et al. | |
| 6,371,370 B2 | 4/2002 | Sadler et al. | |
| 6,406,849 B1 | 6/2002 | Dorsel et al. | |
| 6,770,892 B2 * | 8/2004 | Corson et al. | 250/458.1 |
| 2003/0160181 A1 * | 8/2003 | Corson et al. | 250/458.1 |

OTHER PUBLICATIONS

Agilent G2565AA "Microarray Scnner System with SureScan Technology" User Manuel, Agilent Technologies, May 2002.

* cited by examiner

*Primary Examiner*—Constantine Hannaher

(57) ABSTRACT

A method and system for determining a biopolymer array substrate thickness dependent optimal focus distance for scanning a molecular array by a molecular array scanner are disclosed. Also disclosed are methods of determining the thickness of a biopolymer array substrate using a position sensitive device (PSD) component of a biopolymer array scanner. Further methods include determining the thickness of said biopolymeric array and automatically selecting an optimal focus distance using the determined thickness and a calibration function on thickness versus optimal focus distance. The subject invention finds use in a variety of different applications, including both genomic and proteomic applications.

35 Claims, 14 Drawing Sheets

BIOPOLYMER ARRAY SUBSTRATE THICKNESS DEPENDENT AUTOMATED FOCUS-DISTANCE DETERMINATION METHOD FOR BIOPOLYMER ARRAY SCANNERS

TECHNICAL FIELD

The present invention relates to the biopolymer/molecular array scanners and, in particular, to automated adjustment of the focal distance at which a sample biopolymer/molecular array is positioned with respect to laser light sources and photodetectors to produce optimal data acquisition.

BACKGROUND OF THE INVENTION

The present invention is related to acquisition of biopolymer or molecular-array data and other types of genetic, biochemical, and chemical data from molecular arrays by molecular array scanners. A general background of biopolymer/molecular-array technology is first provided, in this section, to facilitate discussion of the scanning techniques described in following sections.

Array technologies have gained prominence in biological research and are likely to become important and widely used diagnostic tools in the healthcare industry. Currently, molecular-array techniques are most often used to determine the concentrations of particular nucleic-acid polymers in complex sample solutions. Molecular-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of an array. Because arrays are widely used for analysis of nucleic acid samples, the following background information on arrays is introduced in the context of analysis of nucleic acid solutions following a brief background of nucleic acid chemistry.

Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. When phosphorylated, subunits of DNA and RNA molecules are called "nucleotides" and are linked together through phosphodiester bonds 110–115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A DNA nucleotide comprises a purine or pyrimidine base (e.g. adenine 122 of the deoxy-adenylate nucleotide 102), a deoxy-ribose sugar (e.g. deoxy-ribose 124 of the deoxy-adenylate nucleotide 102), and a phosphate group (e.g. phosphate 126) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 128 in a DNA nucleotide. RNA polymers contain uridine nucleosides rather than the deoxy-thymidine nucleosides contained in DNA. The pyrimidine base uracil lacks a methyl group (130 in FIG. 1) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

FIGS. 2A–B illustrate the hydrogen bonding between the purine and pyrimidine bases of two anti-parallel DNA strands. FIG. 2A shows hydrogen bonding between adenine and thymine bases of corresponding adenosine and thymidine subunits, and FIG. 2B shows hydrogen bonding between guanine and cytosine bases of corresponding guanosine and cytosine subunits. Note that there are two hydrogen bonds 202 and 203 in the adenine/thymine base pair, and three hydrogen bonds 204–206 in the guanosine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Two DNA strands linked together by hydrogen bonds forms the familiar helix structure of a double-stranded DNA helix. FIG. 3 illustrates a short section of a DNA double helix 300 comprising a first strand 302 and a second, anti-parallel strand 304. The ribbon-like strands in FIG. 3 represent the deoxyribose and phosphate backbones of the two anti-parallel strands, with hydrogen-bonding purine and pyrimidine base pairs, such as base pair 306, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to reannealing of the DNA duplex.

Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

The ability to denature and renature double-stranded DNA has led to the development of many extremely powerful and discriminating assay technologies for identifying the presence of DNA and RNA polymers having particular base sequences or containing particular base subsequences within complex mixtures of different nucleic acid polymers, other biopolymers, and inorganic and organic chemical compounds. One such methodology is the array-based hybridization assay. FIGS. 4–7 illustrate the principle of the array-based hybridization assay. An array (402 in FIG. 4) comprises a substrate upon which a regular pattern of features are prepared by various manufacturing processes. The array 402 in FIG. 4, and in subsequent FIGS. 5–7, has a grid-like two-dimensional pattern of square features, such as feature 404 shown in the upper left-hand corner of the array. It should be noted that many molecular arrays contain disk-shaped features, rather than round features. Each feature of the array contains a large number of identical oligonucleotides covalently bound to the surface of the feature. These bound oligonucleotides are known as probes. In general, chemically distinct probes are bound to the different features of an array, so that each feature corresponds to a particular nucleotide sequence. In FIGS. 4–6, the principle of array-based hybridization assays is illustrated with respect to the single feature 404 to which a number of identical probes 405–409 are bound. In practice, each feature of the array contains a high density of such probes but, for the sake of clarity, only a subset of these are shown in FIGS. 4–6.

Once an array has been prepared, the array may be exposed to a sample solution of target DNA or RNA molecules (410–413 in FIG. 4) labeled with fluorophores, chemiluminescent compounds, or radioactive atoms 415–418. Labeled target DNA or RNA hybridizes through base pairing interactions to the complementary probe DNA, synthesized on the surface of the array. FIG. 5 shows a number of such target molecules 502–504 hybridized to complementary probes 505–507, which are in turn bound to the surface of the array 402. Targets, such as labeled DNA molecules 508 and 509, that do not contains nucleotide sequences complementary to any of the probes bound to array surface, do not hybridize to generate stable duplexes and, as a result, tend to remain in solution. The sample solution is then rinsed from the surface of the array, washing away any unbound labeled DNA molecules. Finally, the bound labeled DNA molecules are detected via optical or radiometric scanning. FIG. 6 shows labeled target molecules emitting detectable fluorescence, radiation, or other detectable signal. Optical scanning involves exciting labels of bound labeled DNA molecules with electromagnetic radiation of appropriate frequency and detecting fluorescent emissions from the labels, or detecting light emitted from chemiluminescent labels. When radioisotope labels are employed, radiometric scanning can be used to detect the signal emitted from the hybridized features. Additional types of signals are also possible, including electrical signals generated by electrical properties of bound target molecules, magnetic properties of bound target molecules, and other such physical properties of bound target molecules that can produce a detectable signal. Optical, radiometric, or other types of scanning produce an analog or digital representation of the array as shown in FIG. 7, with features to which labeled target molecules are hybridized similar to 706 optically or digitally differentiated from those features to which no labeled DNA molecules are bound. In other words, the analog or digital representation of a scanned array displays positive signals for features to which labeled DNA molecules are hybridized and displays negative features to which no, or an undetectably small number of, labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the array was exposed, of labeled DNA complementary to the oligonucleotide within the feature.

Array-based hybridization techniques allow extremely complex solutions of DNA molecules to be analyzed in a single experiment. An array may contain from hundreds to tens of thousands of different oligonucleotide probes, allowing for the detection of a subset of complementary sequences from a complex pool of different target DNA or RNA polymers. In order to perform different sets of hybridization analyses, arrays containing different sets of bound oligonucleotides are manufactured by any of a number of complex manufacturing techniques. These techniques generally involve synthesizing the oligonucleotides within corresponding features of the array through a series of complex iterative synthetic steps, or depositing oligonucleotides isolated from biological material.

As pointed out above, array-based assays can involve other types of biopolymers, synthetic polymers, and other types of chemical entities. For example, one might attach protein antibodies to features of the array that would bind to soluble labeled antigens in a sample solution. Many other types of chemical assays may be facilitated by array technologies. For example, polysaccharides, glycoproteins, synthetic copolymers, including block copolymers, biopolymer-like polymers with synthetic or derivitized monomers or monomer linkages, and many other types of chemical or biochemical entities may serve as probe and target molecules for array-based analysis. A fundamental principle upon which arrays are based is that of specific recognition, by probe molecules affixed to the array, of target molecules, whether by sequence-mediated binding affinities, binding affinities based on conformational or topological properties of probe and target molecules, or binding affinities based on spatial distribution of electrical charge on the surfaces of target and probe molecules.

An "array", unless a contrary intention appears, includes any one, two or three dimensional arrangement of addressable regions bearing a particular chemical moiety to moieties (for example, biopolymers such as polynucleotide sequences) associated with that region immobilized on an array substrate. An array is "addressable" in that it has multiple regions of different moieties (for example, different polynucleotide sequences) such that a region (a "feature" or "spot" of the array) at a particular predetermined location (an "address") on the array substrate will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and the chemical moiety or mixture of moieties at a given feature. "Hybridizing" and "binding", with respect to polynucleotides, are used interchangeably.

Any given array substrate may carry one, two, four or more collections of array features disposed on a front surface of the array substrate. Depending upon the use, any or all of the collections of array features may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, usually 5.0 μm to 500 μm, and more usually 10 μm to 200 μm. Non-round features may have area ranges equivalent to that of circular features with the foregoing width (diameter) ranges. At least some, or all, of the features may be of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

The array features can have widths (that is, diameter, for a round spot) in the range from a minimum of about 10 μm to a maximum of about 1.0 cm. In embodiments where very small spot sizes or feature sizes are desired, material can be deposited according to the invention in small spots whose width is in the range about 1.0 μm to 1.0 mm, usually about 5.0 μm to 500 μm, and more usually about 10 μm to 200 μm. Features which are not round may have areas equivalent to the area ranges of round features 16 resulting from the foregoing diameter ranges.

Each collection of array features may cover an area of less than 100 cm$^2$, or even less than 50, 10 or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Once the labeled target molecule has been hybridized to the probe on the surface, the array may be scanned by an appropriate technique, such as by optical scanning in cases where the labeling molecule is a fluorophore or by radiometric scanning in cases where the signal is generated through a radioactive decay of labeled target. In the case of optical scanning, more than one fluorophore can be excited, with each different wavelength at which an array is scanned producing a different signal. In optical scanning, it is common to describe the signals produced by scanning in terms of the colors of the wavelengths of light employed for the scan. For example, a red signal is produced by scanning the array with light having a wavelength corresponding to that of visible red light.

Scanning of a feature by an optical scanning device or radiometric scanning device generally produces a scanned image comprising a rectilinear grid of pixels, with each pixel having a corresponding signal intensity. These signal intensities are processed by an array-data-processing program that analyzes data scanned from an array to produce experimental or diagnostic results which are stored in a computer-readable medium, transferred to an intercommunicating entity via electronic signals, printed in a human-readable format, or otherwise made available for further use. Biopolymer/molecular array experiments can indicate precise gene-expression responses of organisms to drugs, other chemical and biological substances, environmental factors, and other effects. Molecular array experiments can also be used to diagnose disease, for gene sequencing, and for analytical chemistry. Processing of molecular array data can produce detailed chemical and biological analyses, disease diagnoses, and other information that can be stored in a computer-readable medium, transferred to an intercommunicating entity via electronic signals, printed in a human-readable format, or otherwise made available for further use.

FIG. 8 illustrates components of a molecular array scanner. Lasers 800a–b emit coherent light that passes through electro-optic modulators ("EOMs") 810a–b with attached polarizers 820a–b. Each EOM and corresponding polarizer together act as a variable optical attenuator. A control signal in the form of a variable voltage is applied to each EOM 810a–b by controller 880. The controller 880 may include a suitably programmed processor, logic circuit, firmware, or a combination of software programs, logic circuits, and firmware. The control signal changes the polarization of the laser light, which alters the intensity of the light that passes through the EOM. In general, laser 800a provides coherent light of a different wavelength than that provided by laser 800b. For example, one laser may provide red light and the other laser may provide green light. The beams may be combined along a path toward a stage 800 by the use of full mirror 851 and dichroic mirror 853. The light from the lasers 800a–b is then transmitted through a dichroic beam splitter 854, reflected off fully reflecting mirror 856, and then focused, using optical components in beam focuser 860, onto a molecular array mounted on a holder 800. Fluorescent light, emitted at two different wavelengths (for example, green light and red light) from features of the molecular array in response to illumination by the laser light, is imaged using the optics in the focuser/scanner 860, and is reflected off mirrors 856 and 854. The two different wavelengths are further separated by a dichroic mirror 858 and are passed to photodetectors 850*a–b*. More optical components (not shown in FIG. 8) may be used between the dichroic mirror and the photodetectors 850*a–b*, such as lenses, pinholes, filters, and fibers. The photodetectors 850*a–b* may be of various different types, including photo-multiplier tubes, charge-coupled devices, and avalanche photodiodes.

A scan system causes a light spot from each laser 800*a–b* to be moved in a regular pattern about the surface of the molecular array. The molecular array is mounted to a stage that can be moved in horizontal and vertical directions to position light from the lasers onto a particular region at the surface of the molecular array, from which region fluorescent emission is passed back to the photodetectors via the optical path described above. An autofocus detector 870 is provided to sense and correct any offset between different regions of the molecular array and the focal plane of the system during scanning. An autofocus system includes detector 870, processor 880, and a motorized adjuster to move the stage in the direction of arrow 896.

The controller 880 receives signals from photodetectors 850*a–b*, called "channels," corresponding to the intensity of the green and red fluorescent light emitted by probe labels excited by the laser light. The controller 880 also receives a signal from autofocus offset detector 870 in order to control stage adjustment, provides the control signal to the EOMs 810*a–b*, and controls the scan system. Controller 880 may also analyze, store, and output data relating to emitted signals received from detectors 850*a–b*.

The dynamic autofocus mechanism, described above, provides a means for maintaining a constant focus distance during scanning of a molecular array. However, any of various different focus distances may be selected to be held constant during a scan. In general, the focus distance must correspond to the depth of focus of the molecular array optics, but, in general, there is one or a small range of optimal focus distances for a particular molecular array scanner.

One parameter that can impact the optimal focus distance is thickness of an array substrate, e.g., glass thickness. The reason that different thicknesses of glass have different optimal focus positions is that a scanner looks "through" the glass. That is, the excitation light passes through a first surface, e.g., the front surface, of the glass and then through an opposing second surface, e.g., the back surface, of the glass where it then excites the molecules on the far side of the second, opposing surface. Even a scanner that detects features on the near/front surface of the glass may require different focus positions if the physical substrate moves closer or further away from the focusing lens as the glass thickness varies.

Designers, manufacturers, and users of molecular arrays have recognized a need for an automated focus-distance optimization method, where the method takes into account the thickness of the biopolymer array substrate, e.g., glass thickness, being scanned.

Relevant Literature

U.S. Pat. Nos. of interest include: 5,091,652; 5,260,578; 5,296,700; 5,324,633; 5,585,639; 5,760,951; 5,763,870; 6,084, 991; 6,130,745; 6,222,664; 6,284,465; 6,329,196; 6,371,370 and 6,406,849.

SUMMARY OF THE INVENTION

The present invention provides an automated method for determining an optimal focus distance for scanning a molecular array by a molecular array scanner, where the method is biopolymer array substrate thickness dependent in that the focus distance determined by the method is determined based in part on the thickness of the array substrate. Blocks of rows of a reference array are automatically scanned over a range of focus distances, or z-positions, to produce data providing a functional relationship between focus distance, or z-position, and measured signal intensities. The data is then processed by an array substrate thickness dependent routine that selects an optimal focus distance for data scans based on array substrate thickness. In calibrating a scanner according to the present invention, two or more reference substrates, e.g., reference arrays or reference members/elements, of different thickness are scanned according to the above protocol to identify an optimal focus distance for each different substrate thickness. Finally a monotonic curve of optimal focus distance versus array substrate thickness, and in most cases a linear fit to the curve, is obtained with the set of optimal focus distances obtained from the set of reference arrays. The coefficients of the fitted curve (slope and intercept for a linear fit) are stored as calibration data in the optical scanner to be used to find the optimal focal distance for each array substrate before the beginning of every scan using that scanner.

The present invention further provides a computer program product for use with an apparatus such as described herein. The program product includes a computer readable storage medium having a computer program stored thereon and which, when loaded into a programmable processor, provides instructions to the processor of that apparatus such that it will execute the procedures required of it to perform a method of the present invention.

The present invention also provides scanners calibrated according to the subject methods, as well as methods of using the subject calibrated scanners, e.g., in genomic and proteomic array based applications, and kits for use in calibrating optical scanners.

DEFINITIONS

Figure 1:
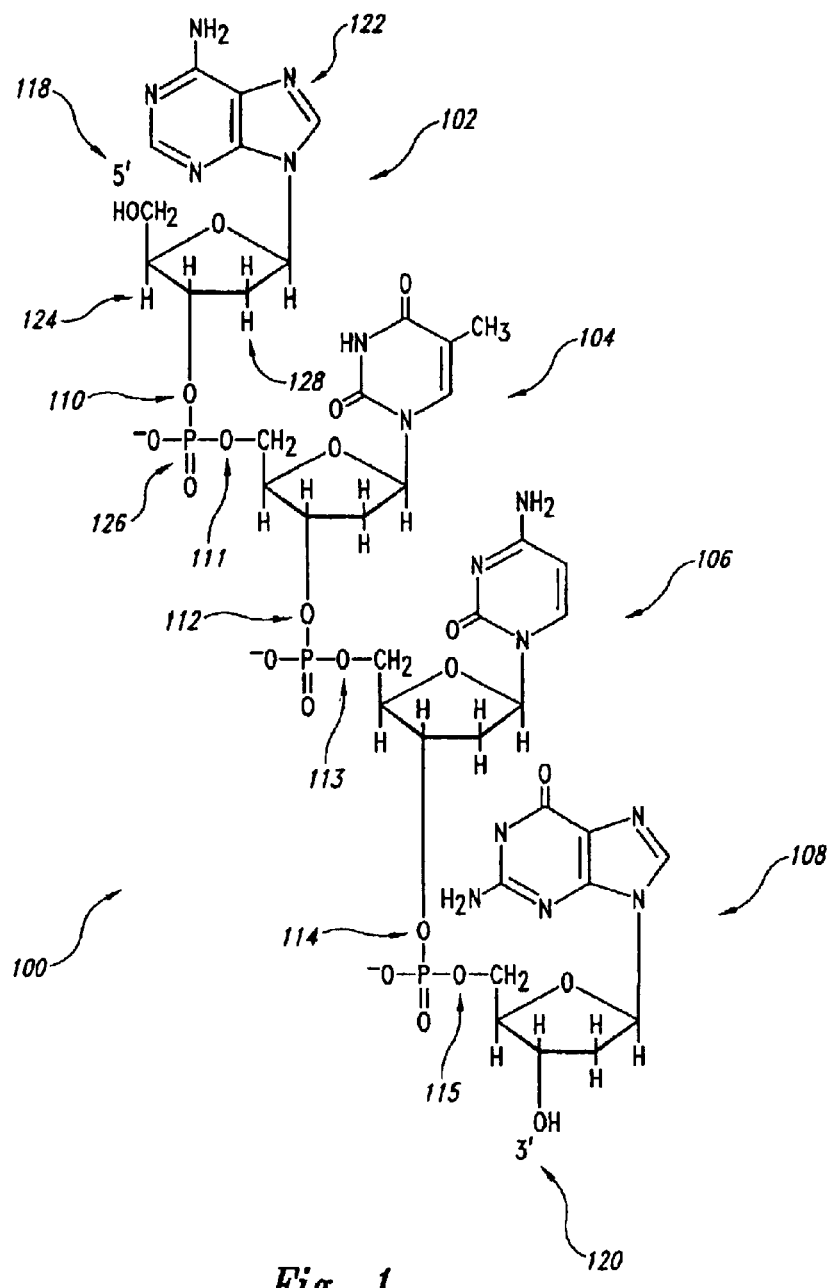
FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108.
Figure 2A:
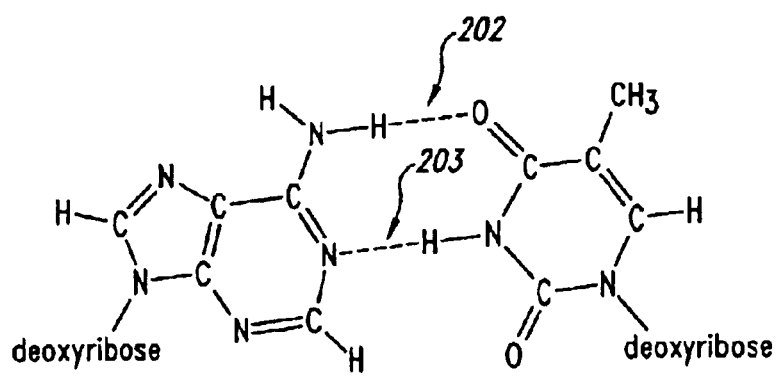
FIGS. 2A–B illustrate the hydrogen bonding between the purine and pyrimidine bases of two anti-parallel DNA strands.
Figure 2B:
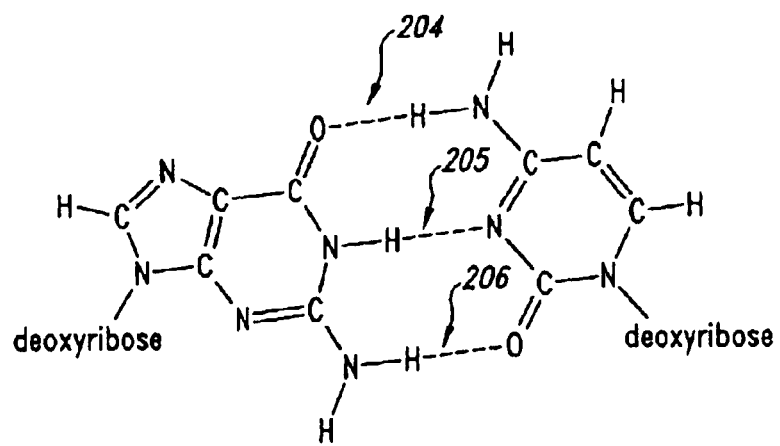
Figure 3:
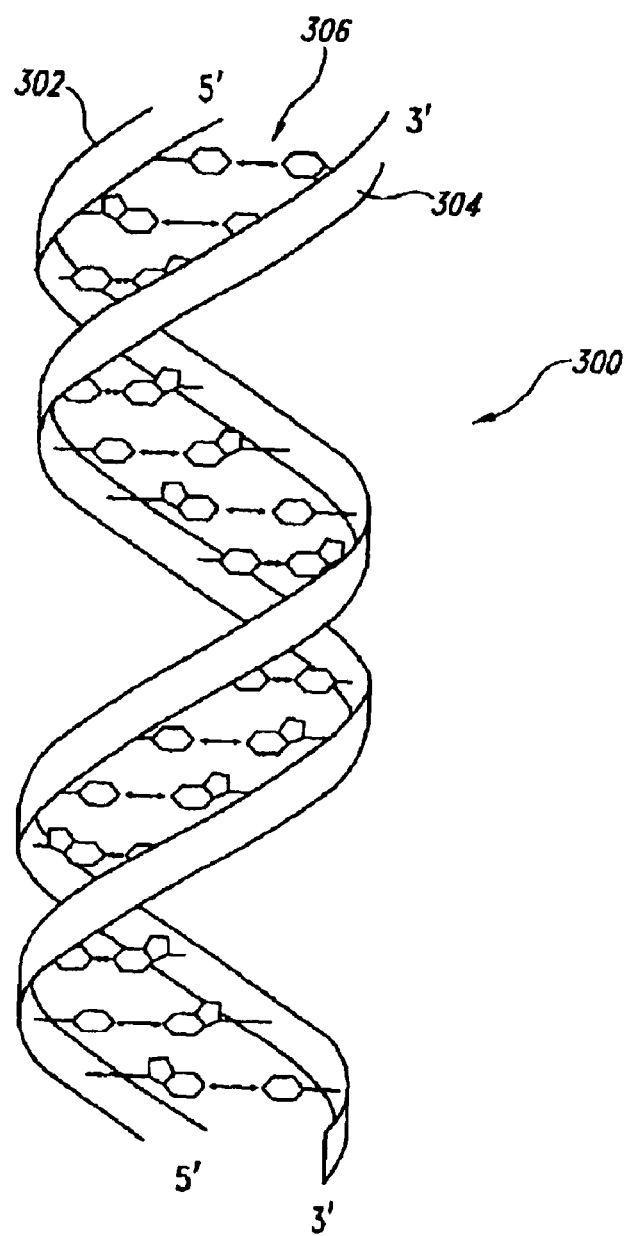
FIG. 3 illustrates a short section of a DNA double helix 300 comprising a first strand 302 and a second, anti-parallel strand 304.
Figure 4:
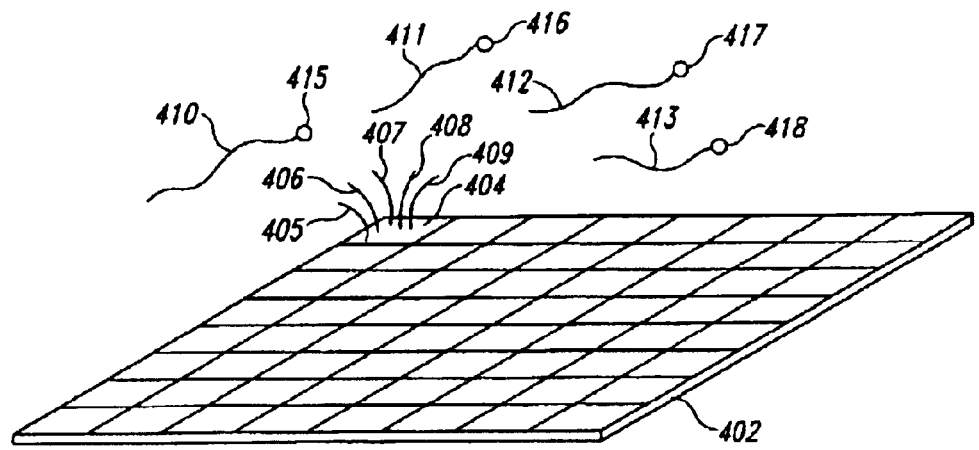
FIGS. 4–7 illustrate the principle of the array-based hybridization assay.
Figure 5:
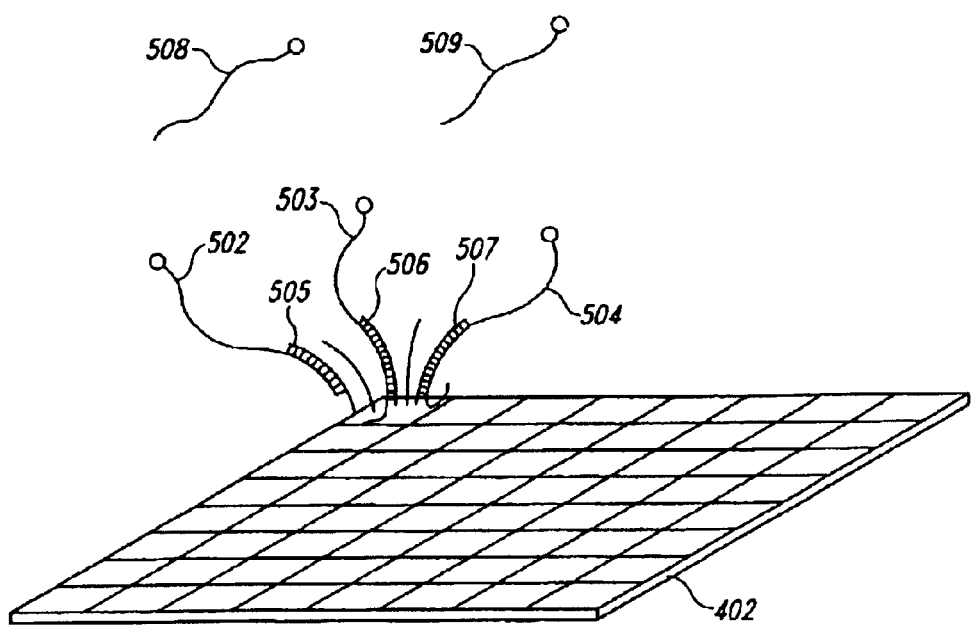
Figure 6:
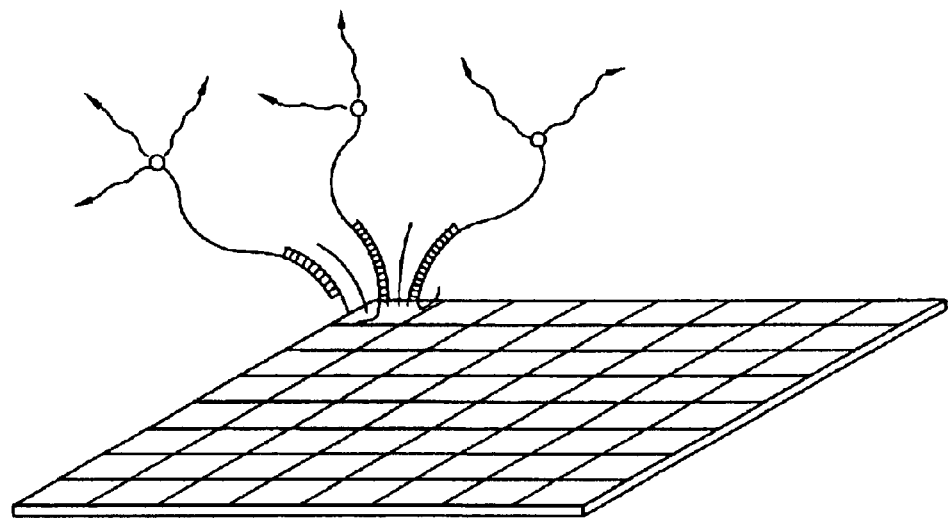
Figure 7:
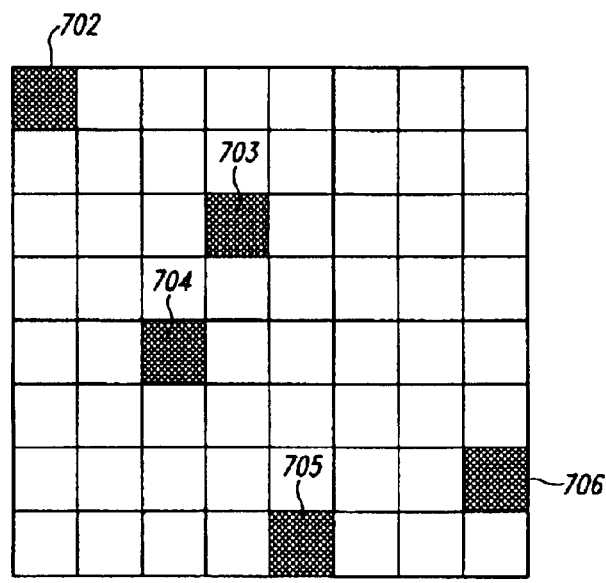
Figure 8:
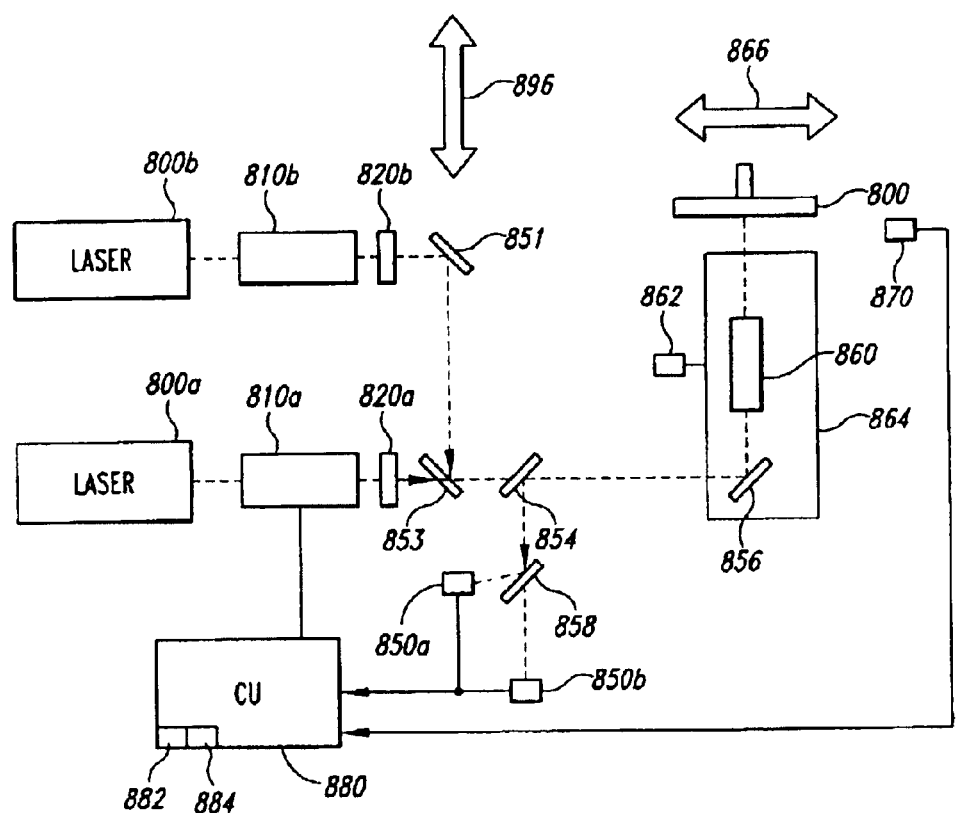
FIG. 8 is a block diagram of major optical and electronic components of a molecular array scanner.

Unless defined otherwise, all technical and scientific terms used herein have the same meaning as commonly understood by one of ordinary skill in the art to which this invention belongs. Still, certain elements are defined below for the sake of clarity and ease of reference.

A "biopolymer" is a polymer of one or more types of repeating units. Biopolymers are typically found in biological systems and particularly include polysaccharides (such as carbohydrates), peptides (which term is used to include polypeptides and proteins) and polynucleotides as well as their analogs such as those compounds composed of or containing amino acid analogs or non-amino acid groups, or nucleotide analogs or non-nucleotide groups. Biopolymers include polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g, a single amino acid or nucleotide with two linking groups one or both of which may have removable protecting groups).

An "array," includes any two-dimensional or substantially two-dimensional (as well as a three-dimensional) arrangement of addressable regions bearing a particular chemical moiety or moieties (e.g., biopolymers such as polynucleotide sequences (nucleic acids), polypeptides (e.g., proteins), etc.) associated with that region. In the broadest sense, the preferred arrays are arrays of polymeric binding agents, where the polymeric binding agents may be any of: polypeptides, proteins, nucleic acids, polysaccharides, synthetic mimetics of such biopolymeric binding agents, etc. In many embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). Sometimes, the arrays are arrays of polypeptides, e.g., proteins or fragments thereof.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 µm to 1.0 cm. In other embodiments each feature may have a width in the range of 1.0 µm to 1.0 mm, usually 5.0 µm to 500 µm, and more usually 10 µm to 200 µm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer or chemical mixture of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. Nos. 6,242,266, 6,232,072, 6,180,351, 6,171,797, 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, photolithographic array fabrication methods may be used such as described in U.S. Pat. Nos. 5,599,695, 5,753,788, and 6,329,143. Interfeature areas need not be present particularly when the arrays are made by photolithographic methods as described in those patents.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (preferably, rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

By "remote location," it is meant a location other than the location at which the array is present and hybridization occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top," "upper," and "lower" are used in a relative sense only.

A "computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

DETAILED DESCRIPTION OF THE INVENTION

An automated calibration method and system for determining a biopolymer array substrate thickness dependent optimal focus distance for scanning a molecular array by a molecular array scanner are provided. In the subject calibration method, blocks of rows of at least two different reference substrates of different thickness are automatically scanned at successively greater distances of the stage from a light gathering medium, such as an optical fiber, or z-positions, to produce data providing a functional relationship between z-position and measured signal intensities. The data for each reference substrate is then processed by an array substrate thickness dependent focus-finding routine that selects an optimal focus-distance for data scans which is optimized for the thickness of the array substrate. The method then determines the equation relating array substrate thickness and optimal focus distance. Then for any given array substrate thickness the optimal focus distance is known, thereby calibrating the optical scanner. In certain embodiments, a function of optimal focus-distance to array substrate thickness is derived from the determined thickness/ optimal focus distance data for reach reference substrate, which function is recorded into the non-volatile memory of the scanner to calibrate the scanner. Also provided are methods of determining the thickness of a biopolymer array substrate using a position sensing detector (PSD) component of a biopolymer array scanner. Also provided are optical scanners calibrated according to the subject invention, as well as methods of using the subject optical scanners in scanning biopolymer/molecular arrays. The subject invention finds use in a variety of different applications, including both genomic and proteomic applications.

Before the invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the invention components which are described in the publications which might be used in connection with the presently described invention.

As summarized above, the subject invention provides methods of calibrating a biopolymer array optical scanner so that the scanner automatically determines an optimal focus distance based on the thickness of the array substrate to be scanned. In further describing the subject invention, the calibration methods are discussed first in greater detail, followed by a review of the optical scanners calibrated according to the subject methods, as well as the a review of the use of such calibrated scanners is various representative applications, including genomic and proteomic applications.

Calibration Methods/Programs

As summarized above, the subject invention provides calibration methods for determining an optimal focus distance at which to scan the surface of a molecular array during data collection from a molecular array by an automated molecular array scanner, where the optimal focus distance determination method is array substrate thickness dependent. By "array substrate thickness dependent" is meant that the optimal focus distance determination method includes the array substrate thickness as a variable, such that the thickness of the array substrate affects the optimal focus distance that is determined using the subject method. More specifically and as described in greater detail below, the specific sub-routine that is employed in the subject methods to determine optimal focus distance is one that is selected based on the substrate thickness of the array that is to be scanned.

For ease of description, the invention is now further described in terms of dynamic autofocus scanner systems. However, even the invention is also useful in static focus scanner systems that "look through" an array substrate, as described above. Therefore, the invention should not be construed as limited to dynamic focus scanner systems.

Dynamic Autofocus

The molecular array scanners of the present invention include dynamic autofocus functionality for maintaining the focus distance at a constant value during scanning of a molecular array. The method for automated array thickness dependent focus-distance determination that represents one embodiment of the present invention may be incorporated into logic circuits, firmware, or software, or a combination of logic circuits, firmware, and software, within the control logic of a molecular scanner.

Figure 9:
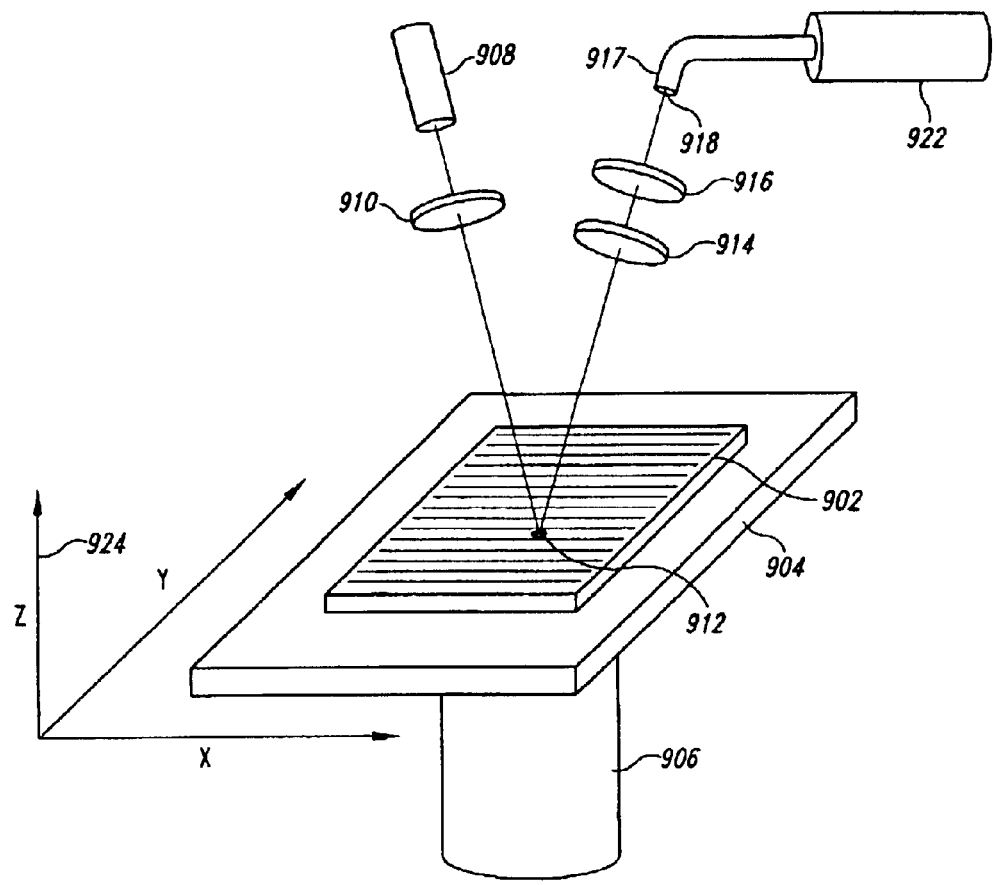
FIG. 9 abstractly illustrates the scanner components related to the automated focus-distance-determination method that represents one embodiment of the present invention.

FIG. 9 abstractly illustrates the scanner components related to the automated focus-distance determination method that represents one embodiment of the present invention. A molecular array 902 is mounted to the stage 904 of a molecular array scanner. The stage 904 can be translated vertically and horizontally in a plane coincident with the plane of the surface of the stage by X and Y translation mechanisms not shown in FIG. 9. In addition, the distance of the stage 904 from the optical fiber or other light-gathering medium can be controlled by a distance-control mechanism that moves the stage and stage support 906 in a direction perpendicular to the plane of the scanner.

Light from a laser 908, focused and filtered via various optic components 910, illuminates a small region of the array 912 from which light of a generally longer wavelength is emitted by fluorescent or chemiluminescent compounds incorporated into target molecules. The emitted light is filtered and focused by various optical components 914 and 916 into a roughly disk-shaped spot 918 that impinges on the surface of an optical fiber 917 or another light-collection medium that inputs emitted light from the surface of the molecular array into a photodetector 922.

An orthogonal x, y, z coordinate system 924 is shown near the left, lower corner of the molecular array-scanner stage 904 to indicate the directions in which the stage can be moved relative to the surface of the optical fiber 917 on which emitted light is focused. The exact functional relationship between variations in the distance from the emitted-light source to the surface of the optical fiber 917, closely related to the distance of the stage from the optical fiber 917, referred to as the z-position of the stage, depends on the geometry of the laser, molecular array, and optical fiber geometries. However, the focus-distance is a continuous function of z-position. If the plane of the surface of the molecular array 902 is not parallel to the plane of the surface of the stage 904, then horizontal translations in the x, y plane of the stage may also affect the distance between light-emitting probe molecules on the surface of the molecular array and the optical fiber 917. The dynamic autofocus feedback-control mechanism within this scanner can dynamically adjust the z-position of the stage as the stage is translated in the x, y plane in order to correct for the small focus-distance variation during a scan due to molecular-array-surface irregularities and positioning and orientation problems that cause the plane of the surface of the molecular array to be inclined with respect to the plane of the surface of the stage. Thus, when an optimal focus-distance is determined, a molecular array can be scanned at this focus distance by the autofocus mechanisms within the scanner. Because the focus distance is a continuous function of the z-coordinate of the spatial location of the illuminated spot 912 of the molecular-array surface, which is, in turn, a continuous function of the z-position of the stage, the following discussion is related to optimizing the z-position of the stage 904. It should be noted that the following discussion and Figures could also be cast in terms of z-coordinate of the laser-illuminated region of a molecular array, or the distance of either the stage or the laser-illuminated region of a molecular array from the emitted-light-collection medium.

Figure 10:
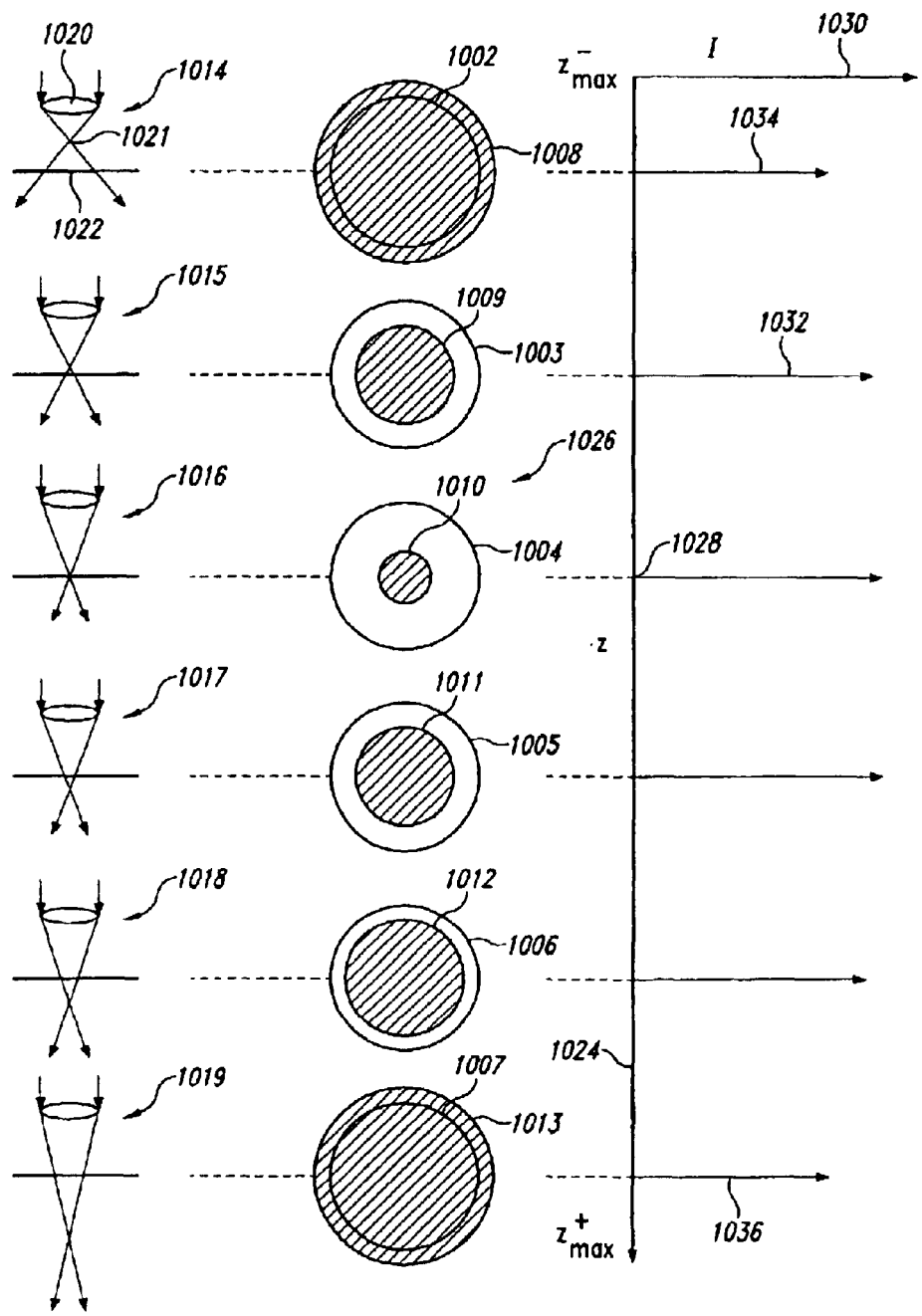
FIG. 10 illustrates the effect of small changes in the z-position of an illuminated spot on the surface of a molecular array with respect to the image of the emitted light from the illuminated spot of the surface of the molecular array focused on the surface of an optical fiber.

FIG. 10 illustrates the effect of small changes in the z-position of the stage, or z-coordinate of an illuminated spot on the surface of a molecular array, with respect to the position of the image of the emitted light from the illuminated spot of the surface of the molecular array focused onto the surface of an optical fiber. This is one example of how the measured intensity of the emitted light can vary with changes in the focal distance. Another example is the loss of emission-intensity due to the lack of correct focus of the illuminated spot on the surface of the molecular array.

In FIG. 10, the circular cross section of the surface of an optical fiber (917 in FIG. 9) is represented by circles 1002–1007. The image of an illuminated spot on the surface of the molecular array of approximately 1.0 mm thickness is shown in FIG. 10 by various differently sized, cross-hatch-filled circles 1008–1013. In FIG. 10, representations 1014–1019 of the focusing of the emitted light onto the plane of the circular cross section of the surface of the optical fiber are shown at the left. In each representation, a lens-like optic, e.g. lens-like optic 1020, focuses light to a point, e.g. point 1021, above, on, or below the plane, e.g. plane 1022, of the surface of the optical fiber. As the illuminated spot on the surface of the molecular array is moved in the z direction, the image of the illuminated spot focused onto the surface of the optical fiber, first defocused as illuminated spot 1008, focuses and decreases in diameter relative to the diameter of the cross section of the optical fiber. Illuminated spot 1010 represents a focused spot, corresponding to the optics representation 1016. As the illuminated spot on the surface of the molecular array is moved further in the z direction, the illuminated spot gradually defocuses and grows in diameter relative to the diameter of the cross section of the optical fiber. At either extreme of the z-position range, as indicated by optics representations 1014 and 1019, the image of the illuminated spot is sufficiently defocused that the image of the illuminated spot is larger than the cross section of the optical fiber, and emission photons representing a portion of the emitted-light are lost, resulting in a decrease in the intensity of the resulting measured signal. In FIG. 10, the z-positions that result in the corresponding respective sizes of the image of the illuminated spot and the cross section of the optical fiber plotted along a coordinate axis 1024 corresponding to the z-position of the stage of the molecular scanner. The z-positions range from a lowest value, $Z_{max}^-$, to a highest z value, $Z_{max}^+$. In FIG. 10, for example, the z-position of the stage resulting in a centered, focused image of the illuminated spot on the surface of the optical fiber 1026 is shown with z coordinate 1028. In FIG. 10, a vertical coordinate axis 1030 is shown orthogonal to the z-position coordinate axis 1024. This orthogonal coordinate axis corresponds to the intensity of the emitted light detected by a photodetector (922 in FIG. 9) of the molecular array scanner. In FIG. 10, the horizontal lines, such as horizontal line 1032, plotted along the vertical z-position axis represent the signal intensities measured for a particular region of the surface of the molecular array corresponding to the z-positions of the stage of the molecular array. Again, as the image of the illuminated region of the molecular array defocuses past the edges of the fiber, not all of the emitted light is captured by the fiber and, as a result, the intensities 1034–1036 of the signal level decreases proportionally to the fraction of light that is missing the fiber.

Figure 11:
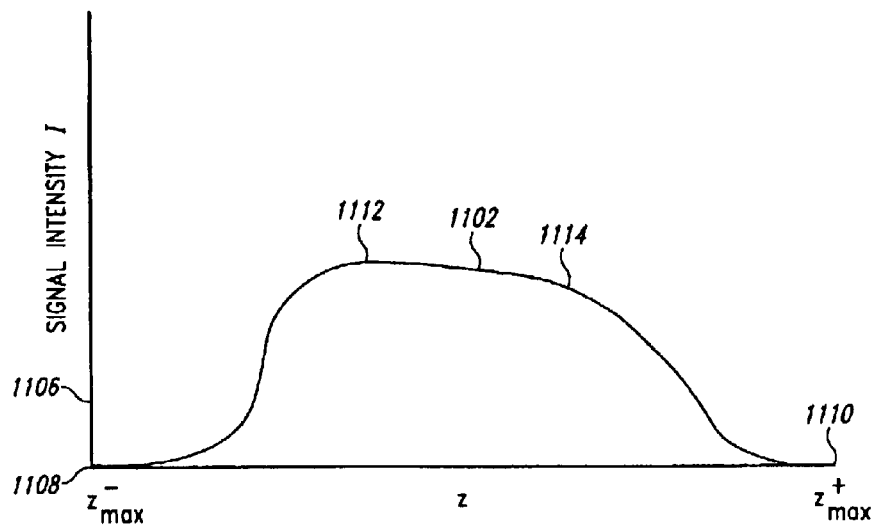
FIG. 11 shows a representation of the function of the signal intensity I measured by the photodetector of a molecular array scanner as a function of the z-position of an illuminated region of the molecular array that generates the signal.

The graph of signal intensity to z-position, as shown in FIG. 10, can be rotated 90 degrees and plotted as a continuous, rather than a discrete, function. FIG. 11 shows a representation of the function of the signal intensity I measured by the photodetector of a molecular array scanner as a function of the z-position of an illuminated region of the molecular array that generates the signal. The function illustrated in FIG. 11 1102 is exaggerated in order to clearly illustrate the general features of a typical signal-intensity-to-z-position ("I/z") relationship for one class of molecular array scanners for array substrates that have an approximately 1.0 mm thickness. As in FIG. 10, the functional relationship is plotted from a $Z_{max}^-$ position to a $Z_{max}^+$ position along the z-position axis 1104, with the height of the curve representing the measured signal intensity with respect to the signal-intensity axis 1106. Proceeding rightward from the $Z_{max}^-$ position 1108 towards to the $Z_{max}^+$ position 1110, the signal intensity sharply rises to a signal intensity peak 1112 and then falls gradually to the edge 1114 of a steeply descending curve that falls back to nearly 0 intensity at $Z_{max}^+$. In one class of molecular array scanners, the I/z function appears as a mesa, with the top of the mesa (section of the curve between 1112 and 1114 in FIG. 11) slanted slightly downward.

Figure 12:
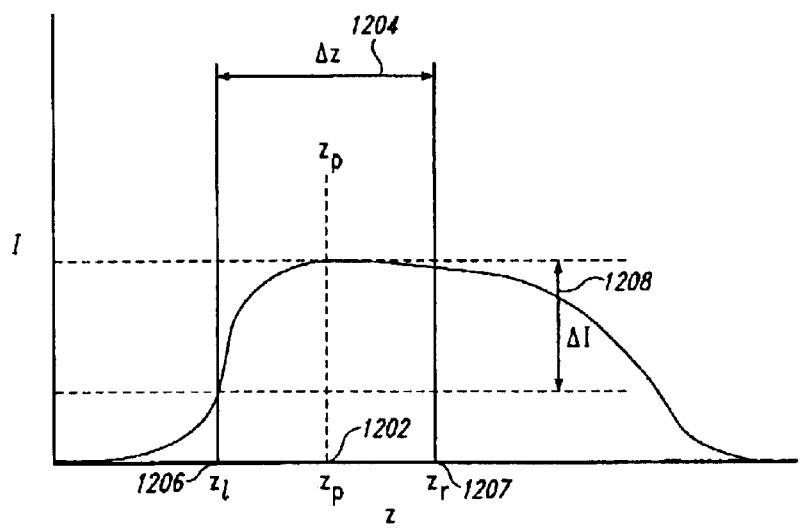
FIG. 12 illustrates the variation in signal intensity I with z-position z in the vicinity of the peak of the $I_z$ curve.

The autofocus mechanism within a molecular array scanner, as with all electromechanical devices, is not infinitely precise. Instead, the autofocus mechanism is capable of maintaining the distance of the illuminated portion of a molecular array surface within a small range of distances by controlling the z-position of the stage. Thus, despite the autofocus mechanism, the z-position, functionally related to the focus distance, varies slightly over the course of a molecular array scan. FIG. 12 illustrates the variation in signal intensity I with z-position z in the vicinity of the peak of the I curve. In FIG. 12, the z coordinate for the peak, $z_p$, is plotted on the z axis 1202. The total variation in z-position during a scan is shown by the interval Δz 1204 plotted from $z_l$ to $z_r$ on the z axis 1206–1207. The signal intensity varies over the interval Δz 1204 by a corresponding signal intensity interval ΔI. Note that, for the typical I/z functional relationship illustrated in FIG. 12, the signal intensity varies over the entire ΔI interval 1208 within the portion of the Δz interval to the left of the peak position $Z_p$, while varying only relatively slightly in the portion of the Δz interval to the right of the peak position $Z_p$. Thus, because of the asymmetry of the I/z curve with respect to the peak position $Z_p$, small fluctuations in the focus distance corresponding to $Z_p$ may result in relatively large variation in signal intensity.

Figure 13:
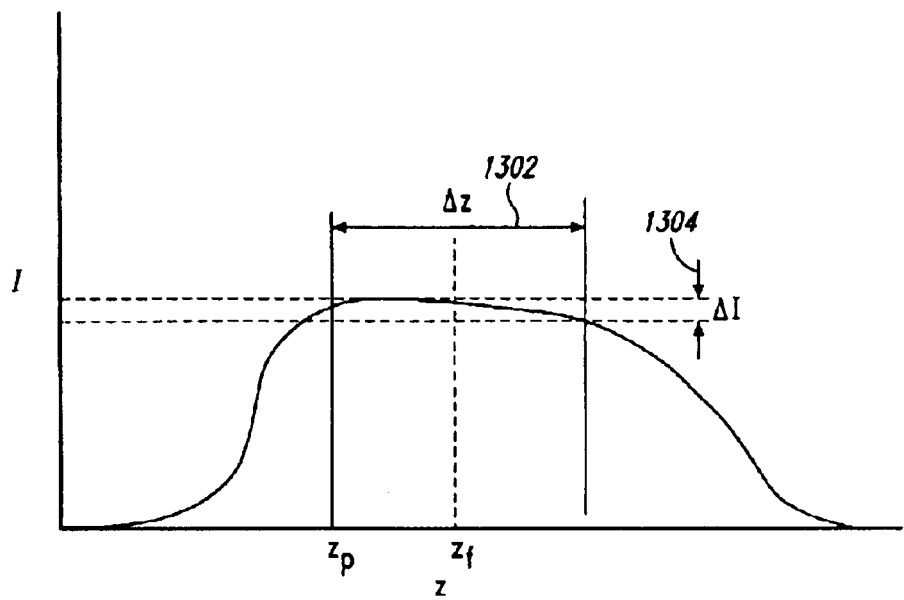
FIG. 13 illustrates selection of an optimal focus distance $Z_p$.

It is desirable to select a focus distance that provides a relatively slight variation in signal intensity corresponding to slight variations in focus distance during scanning of a molecular array. It is the goal of an autofocus mechanism to help maintain a constant system sensitivity for a constant quantity of flurophore over the entire surface of a molecular array. FIG. 13 illustrates selection of an optimal focus distance $Z_f$. As shown in FIG. 13, if the optimal focus distance $Z_f$ is chosen roughly centered in the interval representing the top of the mesa of the I/z curve, producing a $\Delta z$ interval 1302 within the top of the mesa, then the variation in signal intensity $\Delta I$ 1304 over the interval $\Delta z$ is relatively small compared with the $\Delta I$ interval (1208 in FIG. 12) resulting from selection of the focus distance at the peak of the I/z curve $Z_p$.

Figure 14A:
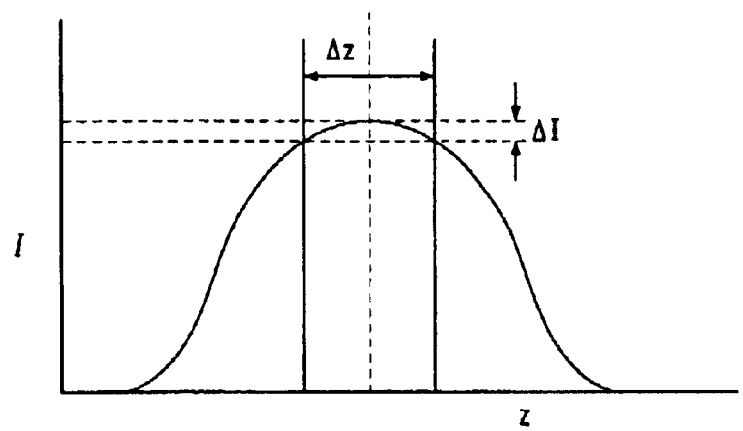
FIG. 14A illustrates the signal intensity variation over a z-position variation centered about the peak of a Gaussian-like I/z curve.
Figure 14B:
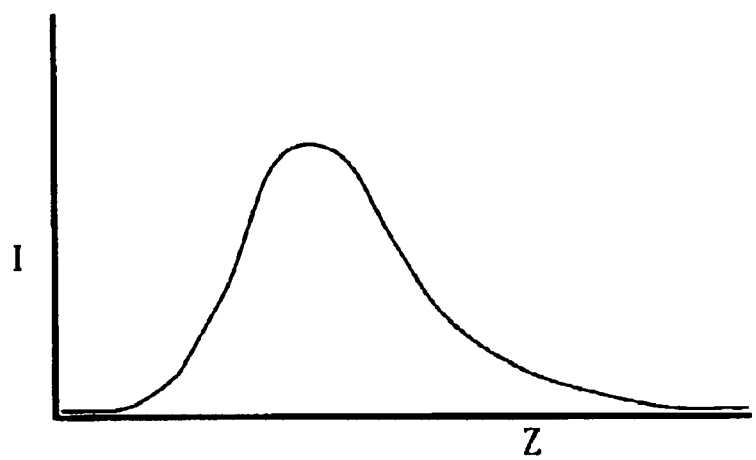
FIG. 14B illustrates the signal intensity variation over a z-position variation centered about the peak of left skewed Gaussian-like I/z curve.

If, by contrast, the scanner geometry and photo-detection apparatus produces a symmetrical, Gaussian-like I/z functional curve, selection of a focus distance corresponding to the z-position of the curve peak $Z_p$ may result in the smallest possible signal intensity variation. FIG. 14A illustrates the signal intensity variation over a z-position variation centered about the peak of the I/z curve. The deviation from the optimum thickness (say 1.0 mm) array substrate may also give rise to a skewed Gaussian-like I/z functional curve, e.g., a left or right skewed curve, as depicted in FIGS. 14B and C, respectively.

As pointed out above, FIGS. 10 to 13 represent the results obtained from an array that has a substrate of approximately 1.0 mm thick, where such an array thickness yields a "mesa" I/z functional curve. For array substrates of other thickness, different results may be obtained. For example, with arrays having substrates of a thickness of about 0.9 mm, a function having a peak but no discernible plateau or mesa configuration is obtained, where the I/z functional curve resembles a leftward skewed Gaussian-like curve, e.g., FIG. 14B. Likewise, with arrays having substrates of a thickness of about 1.2 mm, an I/z functional curve having a peak but no discernible plateau or mesa configuration is obtained, where the I/z functional curve resembles a rightward skewed Gaussian-like curve, e.g., FIG. 14C.

As explained above in the introductory section, the reason that different thicknesses of glass have different optimal focus positions, and therefore different I/z functional curves, is that a scanner looks "through" the glass. That is, the excitation light passes through a first surface, e.g., the front surface, of the glass and then through an opposing second surface, e.g., the back surface, of the glass where it then excites the molecules on the far side of the second, opposing surface. Even a scanner that detects features on the near/front surface of the glass may require different focus positions if the physical substrate moves closer or further away from the focusing lens as the glass thickness varies.

Thickness Dependent Method for Optimal Focus Distance Determination

In the present invention, the particular optimal focus distance that is chosen is one that is determined using a routine selected based on the thickness of the array substrate. Thus, for array substrates having a thickness that generates I/z curves having slanted mesa forms (such as those having a thickness of about 1.0 mm), a routine may be employed in which the focus distance corresponding to a z-position at a positive offset from the peak z-position is selected. Alternatively, for array substrates having a thickness that give rise to a Gaussian-like I/z functional relationship, a routine may be employed in which the focus distance corresponding to the peak z-position, or an average of two points on either side of the peak z-position with a fixed percentage of intensity drop from the peak intensity, may be selected. Whichever method is employed, the optimal focus distance is a focus distance that gives a relatively large signal intensity that varies relatively slightly with variation in the focus distance, where the particular routine employed to determine the optimal focus distance is a routine chosen based on the array substrate thickness.

In the subject calibration methods, one embodiment of the present invention relies on a single-pass, automated scan of two or more reference molecular arrays to calibrate an optical scanner, where the two or more reference substrates, e.g., molecular arrays or reference elements/members, that vary from each other with respect to thickness of their respective substrates. Reference substrates may be substrates prepared by precisely coating the surface of a molecular array substrate of appropriate thickness with a polymethylmethacrylate polymer ("PMMA") containing a fluorescent or chemiluminescent dye. The PMMA polymer can be spun onto the surface of a slide and, if necessary, planarized, using PMMA-substrate-preparation techniques commonly employed in the manufacture of semiconductors. PMMA-based reference substrates are far more uniform than previously employed cyanine-dye reference arrays. U.S. patent application Ser. No. 10/008,598 entitled "Devices For Calibrating Optical Scanners And Methods Of Using The Same" by Holcomb et al. details the PMMA-based reference substrates, and is herein incorporated by reference. The reference substrates employed may be substrates as described in this previously filed invention.

As indicated above, in calibrating a scanner according to the subject invention, two or more reference substrates are scanned, where the reference substrates are of different substrate thickness. The number of reference substrates that are scanned in a typical calibration protocol may vary, so long as a sufficient number is scanned to provide for a meaningful data set to provide for sufficient calibration of the scanner, as described in greater detail below. The number of different reference substrates scanned in a typical calibration may be from 2 to 10, for example 2 to 5. In certain embodiments, the number of reference substrates that are scanned in a typical calibration is 3. The thickness of the reference substrates that are scanned in a calibration may vary, so long as the range of thicknesses as embodiment in the collection of two or more reference substrates is sufficient to provide for adequate calibration of the scanner. In many embodiments, the range of thicknesses scanned in a given calibration is from about 0.75 to 1.5 mm, for example from about 0.8 to 1.25 mm. In certain embodiments, three reference substrates having a thickness of about 0.9, 1.0 and 1.2 are scanned in a given calibration. The difference in thicknesses between any two reference substrates in a set of two or more substrates employed to calibrate a scanner may vary, and in many embodiments ranges from about 0.2 to 5.0 mm, often from about 0.5 to 1.5 mm.

Figure 15:
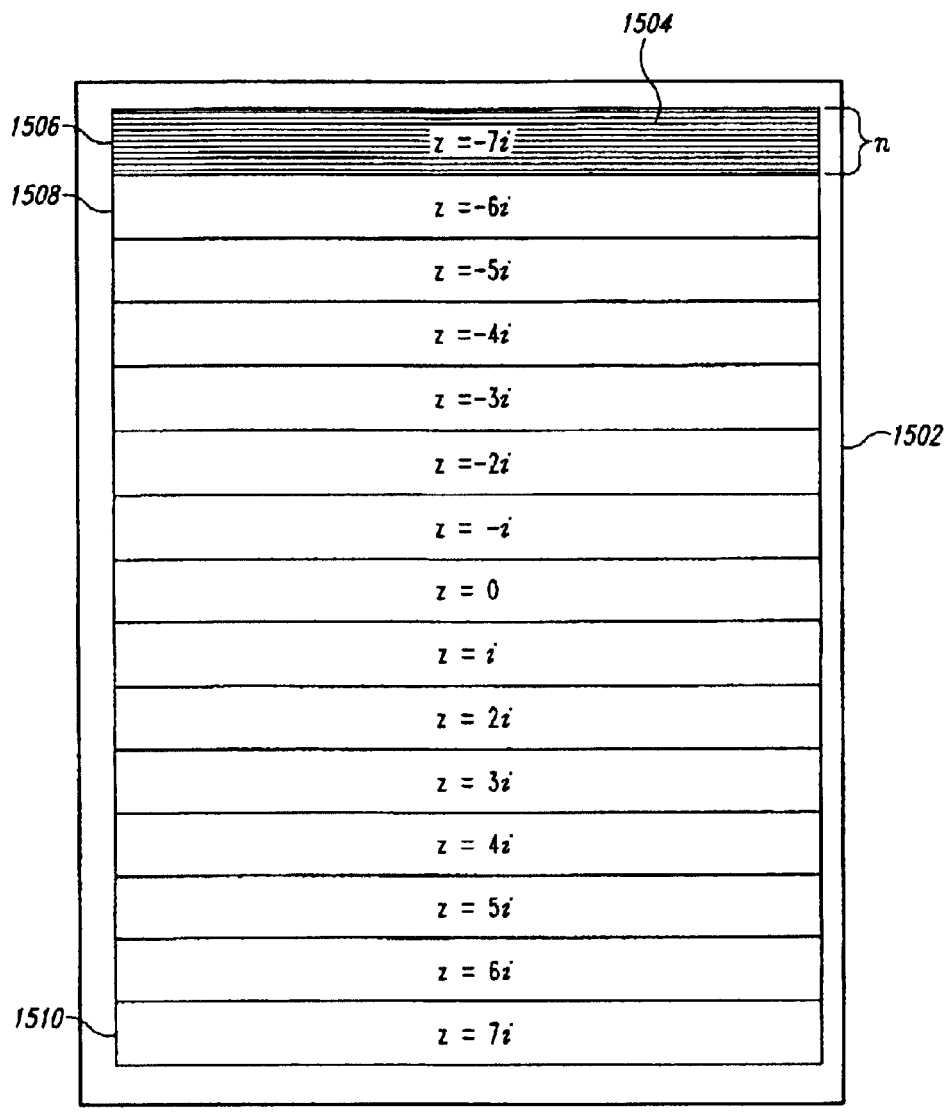
FIG. 15 illustrates the scan pattern employed in a preferred embodiment of the present invention.

In the calibration methods of the subject invention, each reference substrate is scanned to obtain a plurality of signal intensity/focal distance (I/z) data points from which the optimal focus distance for the given reference array is to be chosen. Any convenient scanning protocol that obtains a sufficient set of I/z data points may be employed. FIG. 15 illustrates the scan pattern employed in one embodiment of the present invention. In FIG. 15, a molecular array 1502 is abstractly represented with horizontal rows, such as row 1504. The scan pattern involves scanning a fixed number of contiguous rows n at each z-position over a range of z-positions $Z_{max}^-$ to $Z_{max}^+$. The z-position is incremented by an increment i over this range of z-positions. For example, as shown in FIG. 15, a contiguous block of n rows is first scanned at z-position z=−7i, a second block of n contiguous rows is scanned at z-position z=−6i 1508, and so on, up through scanning of the contiguous block of n rows 1510 at z-position z=7i. The number of rows scanned at each z-position n, the z-position increment i, and the range $Z_{max}^-$ to $Z_{max}^+$ may all be specified in a configuration file for the automated focus-distance determination. Note that there are many alternative possible focus-distance-determination scan patterns. In one embodiment of the present invention, z positions ranging from $-20\mu$ (microns) to $+20\mu$ are scanned at $0.25\mu$ increments, with ten rows scanned for each z-position. The above range is representative and will change for different array substrate thicknesses.

Following collection of a set of I/z data points for a reference substrate as described above, an automated routine or method is employed to automatically determine an optimal focus distance. As discussed above, the particular routine employed is chosen based on the thickness of the reference substrate. In other words, from two or more possible optimal focus distance determination routines, a particular routine is chosen based on the thickness of a given reference substrate. For example, three different routines may be employed in a given calibration method, i.e., routine 1, 2 and 3. If a reference substrate has a thickness of X, then routine 1 may be selected for optimal focus distance determination. Likewise, if a reference substrate has a thickness of Y, then routine 2 may be selected for optimal focus distance determination. Similarly, if a reference substrate has a thickness of Z, then routine 3 may be selected for optimal focus distance determination.

The thickness of a given reference substrate may, in certain embodiments, be predetermined and manually entered into the scanner for use by the calibration routine. Alternatively, where possible, the scanner itself may automatically determine the reference substrate thickness, e.g., by determination of the optical thickness of the reference substrate. In certain embodiments, a position sensing detector (PSD) of the biopolymer array scanner is employed to determine the reference substrate thickness. PSD devices are well known to those of skill in the art, and are further described in U.S. Pat. No. 6,130,745; the disclosure of which is herein incorporated by reference. Where a PSD is employed to determine the thickness of the reference substrate, the first step is to position the reference substrate on a receiving element, e.g., stage, of a biopolymer array scanner. Next, a first position of the receiving element is identified using the auto focus encoder, in which light reflected from a first surface, e.g., a front surface, of the reference substrate is received at a predetermined location of the PSD. Following this step, a second position of the receiving element is similarly identified where light reflected from an opposing second surface, e.g., the back surface, of the reference substrate is received at the same predetermined location of said PSD. The difference between the first and second positions is then determined to obtain the thickness of the reference substrate.

In other words, the difference in auto focus encoder positions is determined when the reflected light signals from the first and second opposing surfaces of the reference substrate hit the same spot on the PSD. The spot on the PSD that is most likely to be hit by the reflection from both the first and second, e.g., front and back, surfaces is the right edge (in one embodiment), and therefore the right edge of the PSD is typically the predetermined location of the PSD that is employed to determine reference substrate thickness. The distance moved by the stage in the horizontal direction between the front and back reflection is referred to as the "optical thickness." The optical thickness of the substrate, e.g., glass substrate, is approximately the physical thickness of the substrate divided by the optical index. Assuming the optical components of the scanner are aligned correctly, the optical thickness of the glass slide should not vary from scanner to scanner. As such, the above PSD based method can be employed readily to determine the thickness of the reference substrate.

While the above described PSD method was described in terms of determining thickness of a reference substrate, it is fully applicable to use in the thickness determination of an array substrate, and such is explicitly encompassed in the scope for the present invention.

As indicated above, the particular optimal focus distance subroutine employed to determine the optimal focus distance for a reference substrate of a given thickness is one that is chosen based on the thickness of the reference substrate, e.g., as determined using the above PSD based protocol.

Figure 16:
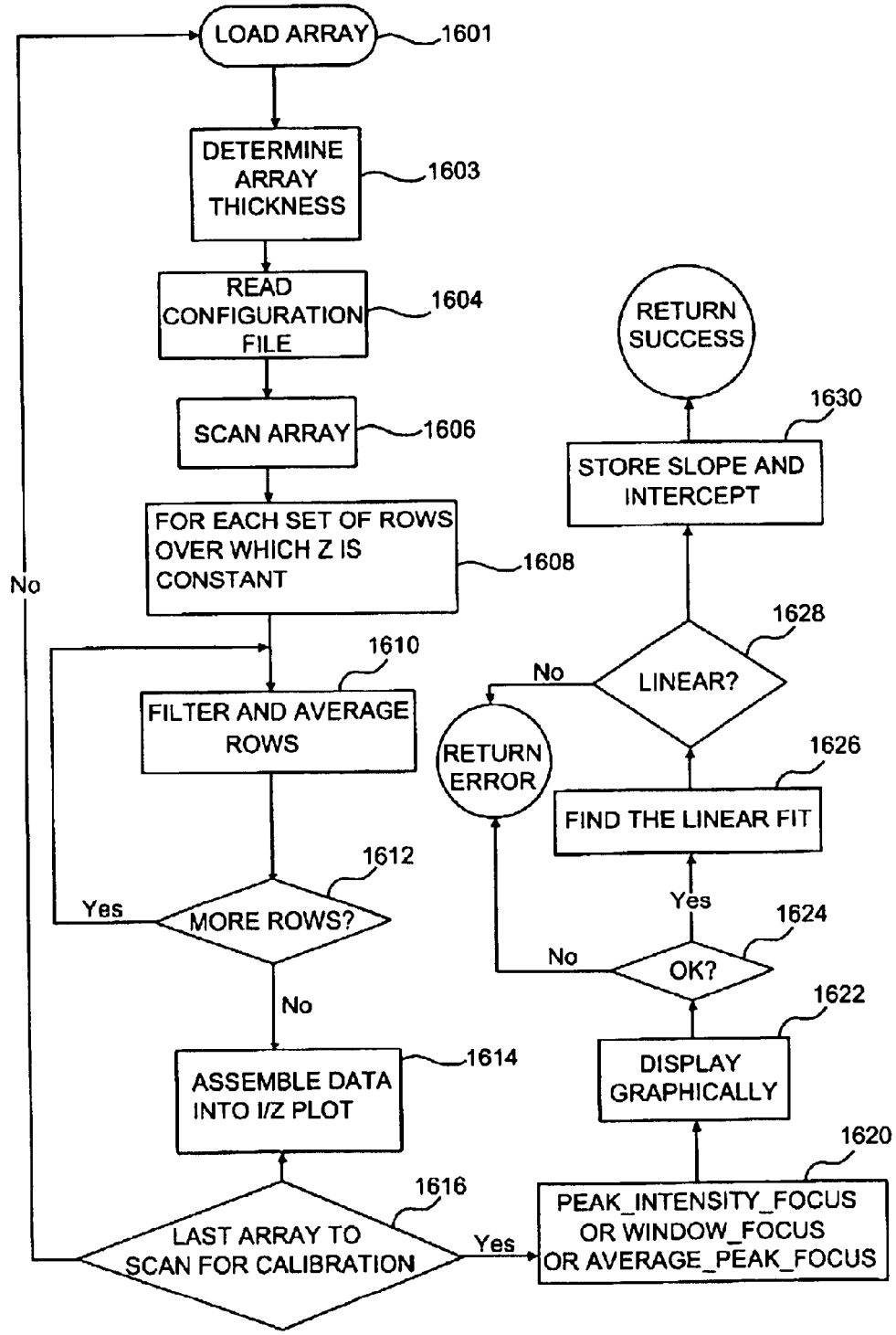
FIG. 16 is a flow-control diagram for determining the calibration parameters of the optimal focus-distance determination method that represents one embodiment of the present invention. The calibration parameters are the slope and the intercept if there is an approximate linear relation between the set of optimal focus distances and the array substrate thicknesses.

Turning now to the calibration routine, FIG. 16 is a flow-control diagram for the optimal focus-distance determination method "focus_distance" that represents one embodiment of the present invention. In step 1602, the scanner is initialized. Initialization involves checking the scanner to make sure that the scanner is properly physically configured, setting the photodetector voltages to default voltages, initializing a stage motion controller(s), and loading the reference substrate into the scanner and verifying, via a barcode imprinted on the surface of the substrate, that the reference substrate is the appropriate reference substrate for the optimal focus-distance determination. In step 1603 the thickness of the reference substrate is determined. This step may involve simply inputting a predetermined thickness into the scanner, or determining the thickness of the substrate contemporaneously, e.g. using the array PSD method as described above. In step 1604, the Intensity/Focal distance curve determination configuration file is input, specifying various parameters including the parameters n, i, $Z_{max}^-$ and $Z_{max}^+$ (based on the optical thickness of the substrate) described with reference to FIG. 15. In step 1606, the reference substrate is scanned as specified by the configuration-file parameters input in step 1604. The reference substrate scan results in a computer encoding of signal intensities measured for discrete regions covering the surface of the substrate. In many molecular array scanners, these signal-intensity results are encoded as integer or floating-point values associated with pixels within the scanned image of the molecular array. In the for-loop comprising steps 1608, 1610, and 1612, focus_distance filters and averages the signal intensities for each block of n rows. The rows are filtered to remove saturated pixels, or, in other words, pixels with intensity values that exceed the linear range of the electronics (due, for example, to dust), and the signal intensities of the remaining pixels are averaged to produce an average intensity value corresponding to the z-position at which the rows were scanned. Note that, if the number of saturated pixels exceeds some specified threshold, the scan may be rejected, and an indication displayed by the molecular array scanner to a user indicating that the molecular array scanner needs to be reconfigured in order to produce signal intensities within appropriate ranges.

Next, in step 1614, the average intensity values for each z-position are assembled into a computer-encoded format corresponding to the I/z graphs shown in FIGS. 11–14, above. Note that each type of signal, such as the red and green signals present in many two channel optical scanners, in the background section, are measured to produce separate I/z functional relationship for each type of signal, or channel. The computer-encoded data representing the I/z functional relationship for each channel can then be scanned with respect to z-position to determine the I and z coordinates of the peak of the I/z curve. In step 1616, a determination is made as to whether the current array is the last array to be scanned for this calibration. If not, the routine returns to step 1601 and the next array is loaded. If the array is the last array, then for each set of I/z data the appropriate focus-finding routine (as described below) is chosen. As mentioned above, the particular focus routine that is called in step 1620 for a particular set of I/z data is one that is selected based on the thickness of the reference array. For reference substrates having a thickness that produces mesa-shaped I/z functional curves (as shown in FIG. 13), e.g., for reference substrates having a thickness that ranges from about 0.95 to about 1.05 mm, e.g., from about 0.975 to about 1.025 mm, the routine "window_focus" may be called (as described in detail in co-pending application Ser. No. 10/086,743 filed on Feb. 28, 2002 the disclosure of which is herein incorporated by reference). In this method, before determining the optimum focus distance, the routine checks whether the z-positions of the I/z peaks for the one or more channels of the scanner fall within an acceptable range of z-position values. If not, then the routine displays an error message indicating the need for resetting the coarse adjustment of the z-component of the autofocus mechanism, or another resetting or reconfiguration of the molecular array scanner, and then returns an error. If all the peaks fall within an acceptable z-position range, then the routine displays the focus distance optimized for all the channels.

Figure 14C:
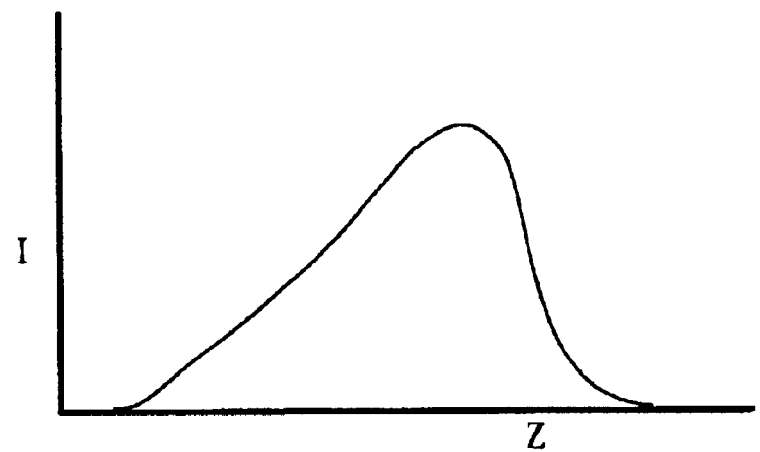
FIG. 14C illustrates the signal intensity variation over a z-position variation centered about the peak of right skewed Gaussian-like I/z curve.

Alternatively, if the thickness of the array gives rise to left or right skewed Gaussian-like curves, e.g., as shown in FIGS. 14B and 14C, the focus routine "average_peak intensity_focus" may be called. Substrate thicknesses that produce other types of I/z curves may need other, specific focus routines. In certain embodiments, if the thickness of a given reference substrate is between about 0.95 and 1.05 mm, e.g., between about 0.975 and 1.025 mm, the routine "window_focus" is employed to determine the optimal focus distance for the reference array. In these particular embodiments, if the thickness is outside of the above range, e.g., below about 0.975 mm (such as about 0.95 mm) or above about 1.025 mm (such as about 1.05 mm) the focus routine "average_peak-intensity-focus" is employed. The focus function called in step 1620 produces optimal z-positions corresponding to optimal focus distances, $Z_f$s, for each channel that can be used by the molecular array scanner for determining the calibration parameters during the manufacturing of a given scanner, as described in greater detail below.

Next, in step 1622, focus_distance graphically displays the intensity versus focus position and results of the optimal focus-distances for each channel and for each substrate used for calibration in separate graphs. The user reviews the displayed information and can input acceptance or rejection of the optimal focus-distances determination. If the method is found to be robust enough for any particular configuration of scanner, this step can be skipped and the process be fully automated. If the optimal focus-distances for all the reference substrates used for calibration are accepted, as determined in step 1624, then in step 1626 an approximate monotonic relation (most ofter linear, can be nonlinear also) is determined between the thickness of the substrate and the optimum focus distance for each channel and for the given set of calibration substrates. Then the parameters for the fitted curve (slope and the intercept for a linear fit) are stored into non-volatile memory within the array scanner in step 1630, and the routine returns success. As indicated above, three representative focus finding routines that may be employed depending on the thickness of a given reference array are: (i) "window_focus"; (ii) "peak_intensity_focus", and (iii) "average_peak_intensity_focus". Each of these particular focus finding routines is now described separately in greater detail.

In the following discussion, the routines are described in terms of a two-channel molecular array scanner that measures emitted light in red and green regions of the visible spectrum. Thus, the following discussion refers to red and green channels and red and green signals. However, the present invention is equally applicable to single-channel molecular array scanners or to molecular array scanners that measure more than two types of signals, or measure signals from different parts of the electromagnetic radiation spectrum.

Window_Focus

One focus-finding routine that finds use in the subject methods, e.g., for reference substrates having a thickness ranging from about 0.95 to 1.05 mm, is the focus-finding routine "window_focus," as called in step 1620 of the routine focus_distance illustrated in FIG. 16. The routine "window_focus" is more suitable for the mesa-shaped I/z curves characteristic of one class of array substrate thickness, as summarized above. The routine "window_focus" is fully described in copending application Ser. No. 10/086,743 filed on Feb. 28, 2002; the disclosure of which is herein incorporated by reference.

Briefly, in this "window-focus-distance" determination method, the routine uses an intensity/position function for each channel of the molecular array scanner. This step is practiced by determining the position of the peak intensity in the intensity/position function for each channel, and returning an error when the positions of peak intensity for each channel do not all fall within a central portion of the range of position.

Next, the routine finds, for each channel, a plateau interval in the intensity/position function for the channel. In this step, for decreasing window intervals sizes, the routine searches window intervals in the position range of the intensity/position function for the channel for a window interval in which intensities differ by less than a threshold value. When a single window interval contains intensities that differ by less than the threshold value, the routine returns the single window interval. When more than one window interval contains intensities that differ by less than a threshold value, the routine selects a window interval having the least difference in intensities and returns the selected window interval. When the current window interval size is less than a minimum window interval size, the routine returns a default window interval.

The routine then finds an overlap position interval that represents overlap in positions from the plateau intervals for each channel. In this step, the routine starts from a center position within the overlap position interval, and then searches outward from the center position to find a small window interval closest to the center position with intensity differences less than a small-window-final-intensity-difference threshold.

When the overlap position interval meets a set of acceptance criteria, the routine finds a focus-distance within the overlap position interval.

Peak_Intensity_Focus

For substrate thicknesses that produce Gaussian-like, roughly symmetrical I/z curves, as shown in FIG. 14A, the focusing routine "peak_intensity_focus" may be called from step 1620 of focus_distance, described with reference to FIG. 16. The routine "peak_intensity_focus" is fully described in copending application Ser. No. 10/086,743 filed on Feb. 28, 2002; the disclosure of which is herein incorporated by reference.

Briefly, in the "peak-intensity-focus" distance determination routine, the routine uses an intensity/position function for each channel of the molecular array scanner. In this step, the routine determines the position of the peak intensity in the intensity/position function, and, starting from the peak-intensity position, moves right and left in position in order to identify a left plateau position and a right plateau position at which the corresponding intensity falls below a threshold value. The routine then selects the positions between the left plateau position and the right plateau position as the plateau interval for the channel. The routine then determines an overlap position interval corresponding to the overlap in position of the plateau intervals of each channel. Finally, when the overlap position interval and plateau for each channel meet acceptance criteria, the routine returns a position within a plateau interval as the focus distance. The acceptance criteria include the overlap position interval having a size greater than an overlap position interval threshold size and the plateau for each channel having a size greater than a plateau threshold size.

Average_Peak_Intensity_Focus

For substrate thicknesses that produce right or left skewed Gaussian-like I/z curves, as shown in FIGS. 14B and C, the focusing routine "average_peak_intensity_focus" may be called from step 1620 of focus_distance, described with reference to FIG. 16. Briefly, in the "average peak-intensity-focus" distance determination routine, the routine uses an intensity/position function for each channel of the molecular array scanner. In this step, the routine determines the position of the peak intensity in the intensity/position function, and, starting from the peak-intensity position, moves right and left in position in order to identify a left threshold position and a right threshold position at which the corresponding intensity falls below a threshold value. The threshold value varies, but is generally more than about 90% of the peak intensity, e.g., more than about 95% of the peak intensity, including 96, 97, 98, and 99% of the peak intensity. The routine then finds the mean of the right and left threshold positions, and the mean is selected as the focus distance.

Figure 17:
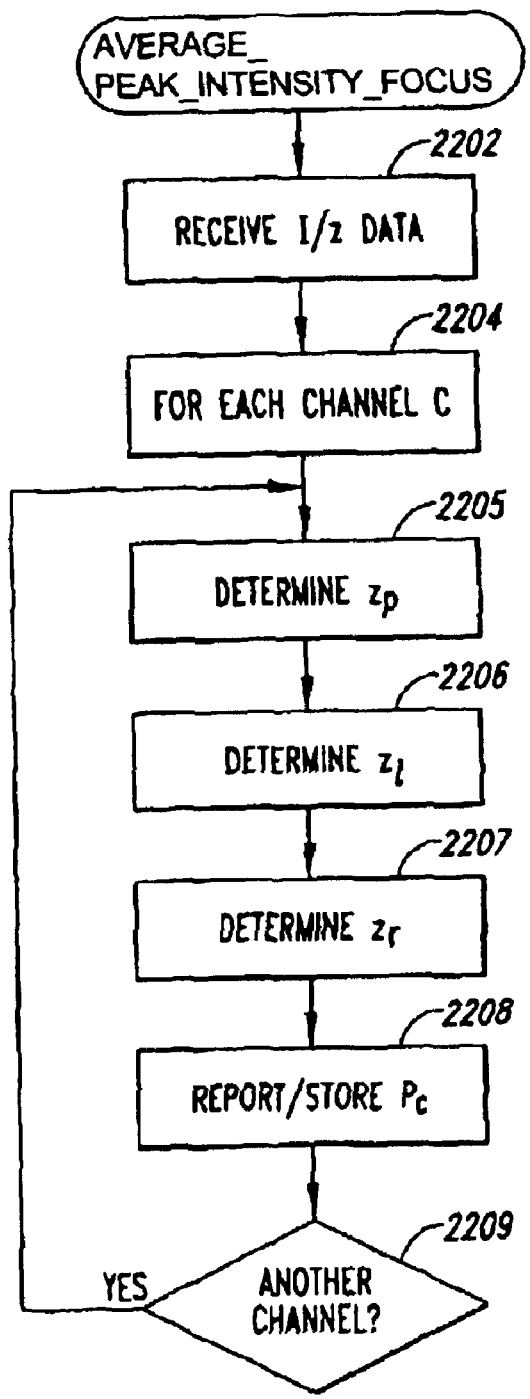
FIG. 17 is a flow-control diagram for the routine "average_peak_intensity_focus."

The routine "average_peak_intensity_focus" is described by the flow-control diagram of FIG. 17. In step 2202, "average_peak_intensity_focus" receives the I/z for each channel scanned by the molecular array scanner. In the for-loop comprising steps 2204–2209, average_peak_intensity_focus determines the peak intensity and right and left threshold positions for each channel. In step 2205, average peak_intensity_focus determines the z-position $Z_p$ corresponding to the peak intensity for the currently considered channel c. In steps 2206 and 2207, peak_intensity_focus determines the $Z_l$ and $Z_r$ z-positions for right and left threshold positions, e.g., positions showing a decrease of 1% from the $Z_p$ intensity, as described above. Then, in step 2208, average_peak_intensity_focus determines the mean of the right and left threshold positions, $Z_r$ and $Z_l$, and reports and stores the mean value $Z_f$ for the currently considered channel c. In step 2209, average_peak_intensity_focus determines whether or not the $Z_f$ for another channel needs to be computed and, if so, control flows back to step 2205. In one embodiment, average_peak_intensity_focus returns the final selected focii $Z_f$s for each channel in step 2209 In other embodiment a single focus distance $Z_f$ can be obtained, which is optimized for all the channels.

Each of the above routines provides an optimal focus distance for each channel for a given reference substrate thickness. In other words, each of the above programs/algorithms provides an optimal focus distance for each channel of a given array substrate thickness. For example, optimal focus distances for three different references substrates and red and green channels, e.g., 0.9 mm thick, 1.0 mm thick and 1.2 mm thick, may be obtained using the appropriate routine from the above selection of three different routines.

Scanner Calibration

The next step in the subject methods is to calibrate the optical scanner. The optical scanner is calibrated by storing a set of at least two optimal focus distance/array substrate thickness data points into the non-volatile memory of the scanner. The optimal focus distance/thickness set of data points may be stored in flash memory, for example, or in other non-volatile memory storage, such as a mass storage device. The set of data points may be stored as a set of discrete data points, e.g., 2, 3, 4 or more data points, including a look up data table, where each data point includes optimal focus distance for a given thickness. In certain embodiments, the set of data points or calibration parameters may also be stored as a continuous function for optimal focus distance versus array substrate thickness, that may be derived from the specific data points determined in the calibration protocol. For example, in one embodiment calibration depth scans are performed three times with reference substrates of thickness 0.9, 1.0 and 1.2 mm during scanner bring up to obtain three pairs of optimal focus distance vs. thickness data points. Each pair consists of one focus distance for red and another for green channels of the optical scanner. The three pairs of data points are then plotted and the slope and intercept of the linear fit are stored in the non-volatile memory of the scanner, e.g., as two new flash values. The stored slope and intercept of the linear fit, representing a continuous function of optical focus distance vs. thickness, are then employed to calculate the optimal focus distances corresponding to the array substrate thicknesses in subsequent data acquisition scans.

Calibration Programming

Calibration programming according to the present invention as described above can be recorded on computer readable media, e.g any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information.

Although the above-described programming has been described in terms of a particular embodiment, it is not intended that the invention be limited to this embodiment. Modifications within the spirit of the invention will be apparent to those skilled in the art. For example, many different scan patterns may be used to construct the I/z data employed by the automated focus-distance determination routines. Different ranges of window sizes may be employed, and different orderings in window searching may be employed. The automated focus-distance determination routines can be implemented in many different languages, or hardware circuits, in an almost limitless number of ways, using different modular organizations and control logic. The methods was generally described in flow-control diagrams to include an arbitrary number of channels, and is intended to be applicable for 1-channel, 2-channel, and many-channel molecular array scanners.

Optical Scanners

Also provided by the subject invention are biopolymer array optical scanners that are programmed/calibrated as described above. Any biopolymer optical scanner or device may be provided to include the above programming. Representative optical scanners of interest include those described in U.S. Pat. Nos.: 5,585,639; 5,760,951; 5,763,870; 6,084,991; 6,222,664; 6,284,465; 6,329,196; 6,371,370 and 6,406,849—the disclosures of which are herein incorporated by reference.

Utility

The subject calibrated biopolymer optical scanners find use in a variety of applications, where such applications are generally analyte detection applications in which the presence of a particular analyte in a given sample is detected at least qualitatively, if not quantitatively. Protocols for carrying out array assays are well known to those of skill in the art and need not be described in great detail here. Generally, the sample suspected of comprising the analyte of interest is contacted with an array under conditions sufficient for the analyte to bind to its respective binding pair member that is present on the array. Thus, if the analyte of interest is present in the sample, it binds to the array at the site of its complementary binding member and a complex is formed on the array surface. The presence of this binding complex on the array surface is then detected, e.g., through use of a signal production system such as a fluorescent label present on the analyte, etc, where detection includes scanning with an optical scanner according to the present invention. The presence of the analyte in the sample is then deduced from the detection of binding complexes on the substrate surface.

Specific analyte detection applications of interest include hybridization assays in which the nucleic acid arrays of the subject invention are employed. In these assays, a sample of target nucleic acids is first prepared, where preparation may include labeling of the target nucleic acids with a label, e.g., a member of signal producing system. Following sample preparation, the sample is contacted with the array under hybridization conditions, whereby complexes are formed between target nucleic acids that are complementary to probe sequences attached to the array surface. The presence of hybridized complexes is then detected. Specific hybridization assays of interest which may be practiced using the subject arrays include: gene discovery assays, differential gene expression analysis assays; nucleic acid sequencing assays, and the like. References describing methods of using arrays in various applications include U.S. Pat. Nos.: 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992—the disclosures of which are herein incorporated by reference.

Where the arrays are arrays of polypeptide binding agents, e.g., protein arrays, specific applications of interest include analyte detection/proteomics applications, including those described in U.S. Pat. Nos.: 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803—the disclosures of which are herein incorporated by reference.

In using an array in connection with a calibrated/programmed scanner according to the present invention, the array will typically be exposed to a sample (such as a fluorescently labeled analyte, e.g., protein containing sample) and the array then read. Reading of the array may be accomplished by illuminating the array and reading the location and intensity of resulting fluorescence at each feature of the array to detect any binding complexes on the surface of the array.

A feature of the subject methods is that at the optimal focus distance employed by the scanner in the array reading step is automatically determined by the scanner based on the thickness of the substrate of the array being read. In certain embodiments, the array is loaded into the scanner and the scanner PSD is employed to determine the array substrate thickness, e.g., by the method described above. In other embodiments, the array substrate thickness is a predetermined value that is input into the scanner. In any event, the particular optimal focus distance employed during the array scan is one that is automatically chosen by the scanner based on the array substrate thickness, e.g., by selecting the appropriate focus distance for the array substrate thickness from the calibration values stored in the non-volatile memory of the scanner.

Results from reading an array may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication) to a remote location if desired, and received there for further use (such as further processing). Stated otherwise, in certain variations, the subject methods may include a step of transmitting data from at least one of the detecting and deriving steps, to a remote location. The data may be transmitted to the remote location for further evaluation and/or use. Any convenient telecommunications means may be employed for transmitting the data, e.g., facsimile, modem, internet, etc.

Kits

Kits for use in connection with the subject invention may also be provided. Such kits preferably include at least a computer readable medium including programming as discussed above and instructions. The instructions may include installation or setup directions. The instructions may include directions for use of the invention with options or combinations of options as described above. In certain embodiments, the instructions include both types of information.

Providing the software and instructions as a kit may serve a number of purposes. The combination may be packaged and purchased as a means of upgrading an existing scanner. Alternately, the combination may be provided in connection with a new scanner in which the software is preloaded on the same. In which case, the instructions will serve as a reference manual (or a part thereof) and the computer readable medium as a backup copy to the preloaded utility.

The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed and/or from which the instructions can be downloaded. Conversely, means may be provided for obtaining the subject programming from a remote source, such as by providing a web address. Still further, the kit may be one in which both the instructions and software are obtained or downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

In addition to the subject calibration programming and instructions, the kits may also include one or more reference substrates, e.g., two or more reference substrates of varying thickness, for use in calibrating an optical scanner during bring up. The reference arrays may be any convenient arrays, such as the reference arrays described above.

Advantages and Features of the Present Invention

In molecular array scanners that include dynamic auto-focus functionality for maintaining the focus distance at a constant value during scanning, assumptions are typically made that the optimal focus position in a particular scanner remains constant for any array substrate thickness within an acceptable range. However, a fixed focus position for the whole range of substrate thickness is not a practical approach. For example, when a 1.2 mm glass is held at the focal plane (which is determined using a 0.98 mm thick glass slide optimized focus position during scanner bring up) a 40% drop in signal intensity is noticed. This decrease is because the surface of the array is no longer being held in the optimal focal plane. Also, since the focus position is not optimal the change in intensity for a given change in the focus position is greater than normal. As such, when small variations in focus position lead to larger changes in intensity, this can cause oscillations in the scanned image intensity.

The above described problem is traced back to the correct focus position, as measured by the position sensitive detector (optical feedback loop), varying with the glass thickness. The problem is a result of optical aberrations in the light collection optics (particularly the lens). The primary aberration is spherical aberration, which corresponds to the focal length varying with how far from the center of the lens the light ray enters. The PSD loop uses light from one particular radius of the lens aperture, but the emitted florescent light is collected over all available radii. This approach causes the correct focus position for different array substrate thicknesses to register as being "shifted" according to the PSD loop which optically measures the focus position of the glass.

In order to address the above problems, the optical design of current scanners are typically optimized for substrate, e.g., glass, thickness of a narrow range, e.g., 1.0 mm glass with a tolerance of ±0.025 mm. Accordingly, in such programmed scanners with a fixed focus distance, scanned image quality suffers for substrate thickness beyond this narrow range.

The above-described invention exploits the monotonic relationship of the focus position with the glass thickness and dynamically adjusts the focus position at the beginning of every scan after measuring the glass "optical thickness" using the PSD signal. This invention enables the users to use glass slides with thickness varying over a wider range without compromising the scanned image quality.

By using the method described in this invention it is possible to achieve desired scan image quality for any substrate thickness within a broader acceptable range. The disclosed invention reduces visible auto-focus related oscillation from the uniformity scan which gets amplified when the depth setting is incorrect.

With respect to the above-described advantages and features, it should be noted that one or more embodiments of the present invention can provide one or more (or other) of the advantages and/or features as described.

It is evident from the above discussion that the above-described invention provides an effective way to calibrate an optical scanner for use with a wide range of array substrate thickness. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for determining a biopolymer array substrate thickness dependent optimal focus distance of a biopolymer array scanner, the method comprising:
   (a) scanning portions of a reference substrate over a range of positions, each position representing a different distance between an illuminated region of the reference substrate and an emitted-light detection component of the scanner, each portion scanned at a different position;
   (b) assembling data collected from scanning the reference substrate into a representation of an intensity/position function; and
   (c) employing an array substrate thickness dependent focus-distance determination method to determine an array substrate thickness dependent optimal focus distance or range of focus distances for said biopolymer array scanner.

2. The method according to claim 1, wherein said method further comprises determining the thickness of said reference substrate to obtain a substrate thickness value employed in said array substrate thickness dependent focus-distance determination method.

3. The method according to claim 2, wherein the thickness of said reference substrate is determined using a position sensing detector (PSD) of said biopolymer array scanner.

4. The method according to claim 1, wherein said method comprises determining an array substrate thickness dependent optimal focus distance or range of focus distances for said biopolymer array scanner for two or more reference substrates of different thickness.

5. The method according to claim 4, wherein said method further comprises determining a calibration function of optimal focus distance versus substrate thickness from said determined array substrate thickness dependent optimal focus distances or ranges of focus distances for said biopolymer array scanner for two or more reference substrates of different thickness.

6. The method according to claim 5, wherein said calibration function is stored in a non-volatile memory storage element of said scanner to produce a calibrated scanner.

7. A calibration function prepared according to the method of claim 5 encoded by one of:
(a) storing said calibration function in a machine readable medium;
(b) transmitting said calibration function over an electronic communications medium;
(c) displaying said calibration function on display device; and
(d) printing said calibration function in a human readable medium.

8. The method according to claim 1, wherein scanning portions of a reference substrate over a range of positions relative to an emitted-light detection component further includes:
for each position,
scanning a set of rows,
filtering the intensity values scanned for each row, and averaging the intensity values for the set of rows into an average intensity value for the position.

9. The method according to claim 1, wherein assembling data collected from scanning the reference substrate into a representation of an intensity/position function further includes associating each position with an average intensity value.

10. The method according to claim 1, wherein employing an array substrate thickness dependent focus-distance determination method to determine an optimal thickness dependent focus distance or range of focus distances comprises employing a method chosen from: (i) a peak-intensity-focus-distance determination method; (ii) a window-focus-distance determination method; and (iii) an average peak-intensity-focus-distance determination method.

11. The method according to claim 10, wherein when said array substrate thickness is between about 0.95 and 1.05 mm, said employed array substrate thickness dependent focus-distance determination method is chosen from: (i) a peak-intensity-focus-distance determination method; and (ii) a window-focus-distance determination method.

12. The method according to claim 11, wherein said employed array substrate thickness dependent focus-distance determination method is a peak-intensity-focus-distance determination method.

13. The method according to claim 11, wherein said employed array substrate thickness dependent focus-distance determination method is a window-focus-distance determination method.

14. The method according to claim 10, wherein when said array substrate thickness is less than about 0.95 mm or greater than about 1.05 mm, said employed array substrate thickness dependent focus-distance determination method is chosen from: (i) a peak-intensity-focus distance determination method; and (ii) an average-peak-intensity-focus-distance determination method.

15. The method according to claim 14, wherein said employed array substrate thickness dependent focus distance determination method is a peak-intensity-focus distance determination method.

16. The method according to claim 14, wherein said employed array substrate thickness dependent focus-distance determination method is an average-peak-intensity-focus-distance determination method.

17. The method according to claim 14, wherein said average peak-intensity-focus-distance determination method comprises:
(a) determining the position of the peak intensity in the intensity/position function;
(b) identifying a left and right threshold position relative to said determined peak intensity position that have an intensity below a threshold value; and
(c) determining the mean of said left and right threshold positions to determine said array substrate dependent optimal focus distance or range of focus distances.

18. A set of computer instructions for carrying out the method of claim 1 encoded by one of:
storing the computer instructions in a machine readable medium;
transmitting the computer instructions over an electronic communications medium; and
printing the computer instructions in a human readable medium.

19. A method of determining a biopolymer array substrate thickness, said method comprising:
(a) positioning said array substrate on a receiving element of a biopolymer array scanner; and
(b) employing a position sensing detector (PSD) of said biopolymer array scanner to determine said biopolymer array substrate thickness.

20. The method according to claim 19, wherein said employing step (b) comprises:
(i) identifying a first position of said receiving element wherein light reflected from a first surface of said array substrate is received at a predetermined location of said PSD;
(ii) identifying a second position of said receiving element wherein light reflected from a second surface of said array is received at said predetermined location of said PSD; and
(iii) determining the difference of said first and second positions to determine said biopolymer array substrate thickness.

21. A biopolymer array scanner comprising:
(a) a probe-molecule excitation system;
(b) an emitted-light photodetection system that produces a signal representative of the emitted-light intensity;
(c) a biopolymer-array-holding stage that holds a biopolymer array for scanning and that can be moved through a range of positions that place an illuminated region of the surface of the biopolymer array at different distances from the emitted-light photodetection system; and
(d) an automated array substrate thickness dependent focus-distance-determination subsystem.

22. The biopolymer array scanner according to claim 21, wherein said automated array substrate thickness dependent focus-distance-determination subsystem is a set of computer instructions for performing a method comprising:
(a) scanning portions of a reference substrate over a range of positions, each position representing a different distance between an illuminated region of the reference substrate and an emitted-light detection component of the scanner, each portion scanned at a different position;
(b) assembling data collected from scanning the reference substrate into a representation of an intensity/position function; and employing an array substrate thickness dependent focus-distance determination method to determine an array substrate thickness dependent optimal focus distance or range of focus distances for said biopolymer array scanner.

23. A calibrated biopolymer array scanner comprising:
   (a) a probe-molecule excitation system;
   (b) an emitted-light photodetection system that produces a signal representative of the emitted-light intensity;
   (c) a biopolymer-array-holding stage that holds a biopolymer array for scanning and that can be moved through a range of positions that place an illuminated region of the surface of the biopolymer array at different distances from the emitted-light photodetection system; and
   (d) a calibration function that selects an optimal focus distance based on an array substrate thickness.

24. The scanner according to claim 23, wherein said calibration function is a calibration function of optimal focus distance versus substrate thickness.

25. A method of assaying a sample, said method comprising:
   (a) contacting said sample with a biopolymeric array of two or more biopolymer ligands immobilized on a surface of a solid support; and
   (b) reading said array with a calibrated biopolymer array optical scanner according to claim 23 to obtain a result.

26. The method according to claim 25, wherein said reading step (b) includes:
   (i) determining the thickness of said biopolymeric array; and
   (ii) automatically selecting an optimal focus distance using said determined thickness and calibration function.

27. The method according to claim 26, wherein said calibration function is a calibration function of optimal focus distance versus substrate thickness.

28. A method of reading a biopolymer array, said method comprising:
   (a) determining said biopolymer array's substrate thickness;
   (b) automatically selecting an optimal focus distance using the determined substrate thickness and a calibration function on substrate thickness versus optimal focus distance; and
   (c) optically reading said biopolymer array to obtain a result using said optimal focus distance.

29. The method according to claim 28, wherein said thickness is determined using the PSD based method according to a method comprising:
   (a) positioning said array substrate on a receiving element of a biopolymer array scanner; and
   (b) employing a position sensing detector (PSD) of said biopolymer array scanner to determine said biopolymer array substrate thickness.

30. The method according to claim 28, wherein said biopolymer array is chosen from a polypeptide array and a nucleic acid array.

31. The method according to claim 28, further comprising transmitting said result from a first location to a second location.

32. The method according to claim 31, where said second location is a remote location.

33. A method comprising receiving data representing said result of a scan obtained by the method of claim 28.

34. A kit for use in a biopolymer array optical scanner, said kit comprising:
   (a) a computer-readable medium according to claim 19; and
   (b) instructions for operating said scanner according to said programming.

35. The kit according to claim 34, wherein said kit further includes at least one reference array.

* * * * *